United States Patent
Shashoua

(10) Patent No.: US 9,295,707 B2
(45) Date of Patent: Mar. 29, 2016

(54) NEUROPROTECTIVE AND NEURORESTORATIVE METHODS AND COMPOSITIONS

(71) Applicant: Angela Shashoua, Brookline, MA (US)

(72) Inventor: Victor E. Shashoua, Brookline, MA (US)

(*) Notice: Subject to any disclaimer, the term of this patent is extended or adjusted under 35 U.S.C. 154(b) by 0 days.

(21) Appl. No.: 13/936,853

(22) Filed: Jul. 8, 2013

(65) Prior Publication Data
US 2014/0018300 A1    Jan. 16, 2014

Related U.S. Application Data

(62) Division of application No. 11/991,210, filed as application No. PCT/US2006/033422 on Aug. 28, 2006, now Pat. No. 8,507,439.

(60) Provisional application No. 60/712,700, filed on Aug. 29, 2005.

(51) Int. Cl.
| | | |
|---|---|---|
| *A61K 38/02* | (2006.01) | |
| *A61K 38/08* | (2006.01) | |
| *A61K 47/48* | (2006.01) | |
| *C07K 5/062* | (2006.01) | |
| *C07K 5/065* | (2006.01) | |
| *C07K 5/072* | (2006.01) | |
| *C07K 5/078* | (2006.01) | |
| *C07K 5/083* | (2006.01) | |
| *C07K 5/087* | (2006.01) | |
| *C07K 5/093* | (2006.01) | |
| *C07K 5/097* | (2006.01) | |
| *C07K 5/103* | (2006.01) | |
| *C07K 5/107* | (2006.01) | |
| *C07K 5/11* | (2006.01) | |
| *C07K 5/113* | (2006.01) | |
| *C07K 7/06* | (2006.01) | |

(52) U.S. Cl.
CPC .............. *A61K 38/02* (2013.01); *A61K 38/08* (2013.01); *A61K 47/48038* (2013.01); *A61K 47/48284* (2013.01); *A61K 47/48384* (2013.01); *A61K 47/48561* (2013.01); *C07K 5/0606* (2013.01); *C07K 5/06026* (2013.01); *C07K 5/06034* (2013.01); *C07K 5/06078* (2013.01); *C07K 5/06104* (2013.01); *C07K 5/06165* (2013.01); *C07K 5/081* (2013.01); *C07K 5/0808* (2013.01); *C07K 5/0812* (2013.01); *C07K 5/0819* (2013.01); *C07K 5/0821* (2013.01); *C07K 5/101* (2013.01); *C07K 5/1013* (2013.01); *C07K 5/1016* (2013.01); *C07K 5/1019* (2013.01); *C07K 5/1021* (2013.01); *C07K 7/06* (2013.01)

(58) Field of Classification Search
None
See application file for complete search history.

(56) References Cited

U.S. PATENT DOCUMENTS

| | | |
|---|---|---|
| 6,187,906 B1 | 2/2001 | Gluckman et al. |
| 6,890,896 B1 | 5/2005 | Shashoua |
| 7,524,819 B2 | 4/2009 | Shashoua |
| 8,507,439 B2 | 8/2013 | Shashoua |
| 2005/0090446 A1 | 4/2005 | Shashoua |
| 2005/0130881 A1 | 6/2005 | Shashoua |
| 2005/0130902 A1 | 6/2005 | Shashoua |
| 2006/0019901 A1 | 1/2006 | Shashoua |
| 2007/0042962 A1 | 2/2007 | Adams et al. |
| 2009/0082281 A1 | 3/2009 | Shashoua |

FOREIGN PATENT DOCUMENTS

| | | |
|---|---|---|
| AU | 2005201745 A1 | 5/2005 |
| WO | WO 99/40112 A1 | 8/1999 |
| WO | WO 01/36454 A1 | 5/2001 |
| WO | WO 02/092781 A2 | 11/2002 |
| WO | WO 02/096360 A2 | 12/2002 |
| WO | WO 03/066814 A2 | 8/2003 |
| WO | WO 03/070755 A2 | 8/2003 |
| WO | WO 2004/037851 A2 | 5/2004 |
| WO | WO 2004/084809 A2 | 10/2004 |
| WO | WO 2006/101909 A2 | 8/2006 |
| WO | WO 2006/101910 A2 | 8/2006 |
| WO | WO 2007/027559 A2 | 3/2007 |

OTHER PUBLICATIONS

Agholme et al., Journal of Alzheimer's Disease, (20), 4, 1069-1082, Aug. 10, 2010.*
Anantharam et al., Caspase-3-dependent proteolytic cleavage of protein kinase Cdelta is essential for oxidative stress-mediated dopaminergic cell death after exposure to methylcyclopentadienyl manganese tricarbonyl. J Neurosci. Mar. 1, 2002;22(5):1738-51.
Barut et al., The neuroprotective effects of z-DEVD.fmk, a caspase-3 inhibitor, on traumatic spinal cord injury in rats. Surg Neurol. Sep. 2005;64(3):213-20; discussion 220. Abstract Only.
Chan et al., MK-801 temporarily prevents MPTP-induced acute dopamine depletion and MPP+ elimination in the mouse striatum. J Pharmacol Exp Ther. Dec. 1993;267(3):1515-20.
Dawson et al., Molecular pathways of neurodegeneration in Parkinson's disease. Science: Oct. 31, 2003;302(5646):819-22.
Dietz, G.P.H. et al., Delivery of bioactive molecules into the cell: the Trojan horse approach. Mol Cell Neurosci. Oct. 2004;27(2):85-131. Review.
Faden et al., Novel neuroprotective tripeptides and dipeptides. Ann N Y Acad Sci. Aug. 2005;1053 :472-81.
Freyaldenhoven et al., MPTP- and MPP(+)-induced effects on body temperature exhibit age- and strain-dependence in mice. Brain Res. Aug. 7, 1995;688(1-2):161-70.
Freyaldenhoven et al., The dopamine-depleting effects of 1-methyl-4-phenyl-1,2,3,6-tetrahydropyridine in CD-1 mice are gender-dependent. Brain Res. Oct. 7, 1996;735(2):232-8.

(Continued)

*Primary Examiner* — Daniel E Kolker
*Assistant Examiner* — Stacey N MacFarlane
(74) *Attorney, Agent, or Firm* — Wolf, Greenfield & Sacks, P.C.

(57) ABSTRACT

The invention relates to methods and products for preventing and treating neuronal cell death-associated diseases and/or conditions. The products and methods are useful for research and for clinical applications relating to neuronal cell-death associated diseases and/or conditions.

16 Claims, 2 Drawing Sheets

(56) References Cited

OTHER PUBLICATIONS

Fulop, L. et al., Beta-amyloid-derived pentapeptide RIIGLa inhibits Abeta(1-42) aggregation and toxicity. Biochem Biophys Res Commun. Nov. 5, 2004;324(1):64-9.

Gauthier et al., Anatomical and biochemical basis of the extrapyramidal disorders. Prog Neuropsychopharmacol Biol Psychiatry. 1982;6(4-6):595-9.

Glazner, G.W. et al., Nuclear factor-kappaB mediates the cell survival-promoting action of activity-dependent neurotrophic factor peptide-9. J Neurochem. Jul. 2000;75(1):101-8.

Goldberg et al., Combined oxygen and glucose deprivation in cortical cell culture: calcium-dependent and calcium-independent mechanisms of neuronal injury. J Neurosci. Aug. 1993; 13(8):3510-24.

Gozes, I. Neuroprotective peptide drug delivery and development: potential new therapeutics. Trends Neurosci. Dec. 2001;24(12):700-5. Review.

Hashimoto, Y. et al., Detailed characterization of neuroprotection by a rescue factor humanin against various Alzheimer's disease-relevant insults. J Neurosci. Dec. 1, 2001;21(23):9235-45.

He et al., Genome-wide analysis of mRNAs regulated by the nonsense-mediated and 5' to 3' mRNA decay pathways in yeast. Mol Cell. Dec. 2003;12(6):1439-52.

Jenner et al., Understanding cell death in Parkinson's disease. Ann Neurol. Sep. 1998;44(3 Suppl 1):S72-84. Abstract Only.

Kanthasamy et al., Antimyoclonic effect of gabapentin in a posthypoxic animal model of myoclonus. Eur J Pharmacol. Feb. 22, 1996;297(3):219-24.

Kanthasamy et al., Cyanide-induced increases in plasma catecholamines: relationship to acute toxicity. Neurotoxicology. 1991 Winter;12(4):777-84. Abstract Only.

Kanthasamy et al., Dopaminergic neurotoxicity of cyanide: neurochemical, histological, and behavioral characterization. Toxicol Appl Pharmacol. May 1994;126(1):156-63.

Kanthasamy et al., Neuroprotective effects of the strychnine-insensitive glycine site NMDA antagonist (R)-HA-966 in an experimental model of Parkinson's disease. Brain Res. Jun. 6, 1997;759(1):1-8.

Kaul et al., Caspase-3 dependent proteolytic activation of protein kinase C delta mediates and regulates l-methyl-4-phenylpyridinium (MPP+)-induced apoptotic cell death in dopaminergic cells: relevance to oxidative stress in dopaminergic degeneration. Eur J Neurosci. Sep. 2003;18(6):1387-401.

Kosik, Alzheimer's disease: a cell biological perspective. Science. May 8, 1992;256(5058):780-3.

Lambert et al., Beta/A4-evoked degeneration of differentiated SH-SY5Y human neuroblastoma cells, J Neurosci Res. Nov. 1, 1994;39(4):377-85.

Meador et al., Target enzyme recognition by calmodulin: 2.4 A structure of a calmodulin-peptide complex. Science. Aug. 28, 1992;257(5074):1251-5.

Packer et al., Neuroprotection by the metabolic antioxidant alpha-lipoic acid. Free Radic Biol Med. 1997;22(1-2):359-78.

Sasongko et al., Imaging P-glycoprotein Transport Activity at the Human Blood-brain Barrier with Positron Emission Tomography. Clin Pharm Ther. Jun. 2005;77(6):503-514.

Selkoe, Physiological production of the beta-amyloid protein and the mechanism of Alzheimer's disease. Trends Neurosci. Oct. 1993;16(10):403-9.

Sharkey, J. et al., Calcineurin inhibitors as neuroprotectants. CNS Drugs. Jan. 2000;13(1):1-13.

Shashoua et al., CMX-8933, a peptide fragment of the glycoprotein ependymin, promotes activation of AP-1 transcription factor in mouse neuroblastoma and rat cortical cell cultures. Neurosci Lett. Oct. 19, 2001;312(2):103-7.

Shashoua et al., Gamma-aminobutyric acid esters. 1. Synthesis, brain uptake, and pharmacological studies of aliphatic and steroid esters of gamma-aminobutyric acid. J Med Chem. May 1984;27(5):659-64.

Shashoua et al., N-docosahexaenoyl, 3 hydroxytyramine: a dopaminergic compound that penetrates the blood-brain barrier and suppresses appetite. Life Sci. 1996;58(16):1347-57. Abstract Only.

Shashoua et al., Neuroprotective effects of a new synthetic peptide, CMX-9236, in in vitro and in vivo models of cerebral ischemia. Brain Res. Feb. 14, 2003;963(1-2):214-23.

Shashoua et al., New synthetic peptides can enhance gene expression of key antioxidant defense enzymes in vitro and in vivo. Brain Res. Oct. 22, 2004;1024(1-2):34-43.

Shashoua, Ependymin, a brain extracellular glycoprotein, and CNS plasticity. Ann N Y Acad Sci. 1991;627:94-114.

Sherer et al., Environment, mitochondria, and Parkinson's disease. Neuroscientist. Jun. 2002;8(3):192-7.

Stull, N. D. et al., Antioxidant compounds protect dopamine neurons from death due to oxidative stress in vitro. Brain Res. Mar. 29, 2002;931(2):181-5.

Vanden Hoek, T.L. et al., Reperfusion, not simulated ischemia, initiates intrinsic apoptosis injury in chick cardiomyocytes. Am J Physiol Heart Circ Physiol. Jan. 2003;284(1):H141-50. Epub Oct. 10, 2002.

Vila et al., Targeting programmed cell death in neurodegenerative diseases. Nat Rev Neurosci. May 2003;4(5):365-75.

Yankner et al., Neurotrophic and neurotoxic effects of amyloid beta protein: reversal by tachykinin neuropeptides. Science. Oct. 12, 1990;250(4978):279-82.

Zhang et al., Oxidative stress and genetics in the pathogenesis of Parkinson's disease. Neurobiol Dis. Aug. 2000;7(4):240-50. Abstract Only.

* cited by examiner

NEUROPROTECTIVE AND NEURORESTORATIVE METHODS AND COMPOSITIONS

RELATED APPLICATIONS

This application is a divisional of U.S. application Ser. No. 11/991,210, filed Feb. 25, 2010, which is a national stage filing under 35 U.S.C. §371 of international application PCT/US2006/033422, filed Aug. 28, 2006, which was published under PCT Article 21(2) in English, and claims the benefit under 35 U.S.C. §119(e) of U.S. provisional application 60/712,700 filed Aug. 29, 2005, the disclosures of which are incorporated in their entirety herein by reference.

FIELD OF THE INVENTION

The invention relates to peptides that are useful in preventing and/or treating neuronal cell death-associated diseases and/or conditions such as Parkinson's disease (PD) and Alzheimer's disease (AD).

BACKGROUND OF THE INVENTION

Parkinson's disease (PD) affects 0.1% of the population that is older than 40 years of age (Dawson, T. M. and Dawson, V. L. *Science*. (2003) 302(5646):819-822). It is a neurodegenerative condition with symptoms of motor dysfunctions (bradykinesia, tremors, and disturbance in balance) accompanied by variable cognitive impairment. These characteristics are attributed to a large reduction in striatal dopamine content and a loss of dopaminergic (DA) neurons in substantia nigra pars compacta (Gauthier, S. and Sourkes, T. L *Prog Neuropsychopharmacol Biol Psychiatry*. (1982) 6(4-6):595-599). The clinical signs of PD appear after DA neuronal death exceeds a threshold of 70-80% and a loss of striatal nerve terminals that exceed 50-60% (Agid, Y., *Lancet*. (1991) 337 (8753):1321-1324). Investigations of the mechanism of development of PD have indicated that the loss of DA neurons in substantia nigra pars compacta is related to deficits in mitochondrial complex-1 (Jenner, P. and Olanow, C. W. *Ann Neurol*. (1998) (3 Suppl 1):S72-84; Zhang, Y. et al., *Neurobiol Dis*. (2000) August; 7(4):240-250; Sherer, T. B. et al., *Neuroscientist*. (2002) June; 8(3):192-197). A tissue culture model system has been developed that employs the neurotoxin MPP (1 methoyl-4-phenyl-pyridium), (Kaul, S. et al., *Eur J Neurosci*. (2003) 18(6):1387-1401); the metabolite of MPTP (1-methyl-4-phenyl-1,2,3,6-tetrahydro-pyridium) that inhibits complex-1 in mitochondria. The model replicates most of the features associated with sporadic PD syndrome. In the N27 dopaminergic cells (Kaul, S. et al., *Eur J Neurosci*. (2003) 18(6):1387-1401; Anantharam, V. et al., *J Neurosci*. (2002) 22(5):1738-1751) MPP+ generates reactive oxygen species that promote cytochrome c release and caspase-9 and casepase-3 activation that can lead to apoptosis followed by necrosis and inflammation (Dawson, T. M. and Dawson, V. L. *Science*. (2003) 302(5646):819-822).

SUMMARY OF THE INVENTION

It has now been discovered that surprisingly, certain small peptides, protected and non-protected, can be used to prevent and/or treat neurological diseases and/or conditions that are associated with neuronal cell death. Peptide sequences have been identified that act as neuroprotective and/or neurorestorative agents to inhibit and reduce neuronal cell death. These newly identified peptides may be used in the prevention and/or treatment of disease and conditions associated with neuronal cell death, including, but not limited to Parkinson's disease and brain injury. The peptides of the invention may also be useful for research purposes such as development of animal models for diseases associated with neuronal cell death, etc.

The purpose of this invention is to use the identified peptides, protected or unprotected, to treat diseases and/or conditions associated with neuronal cell death, including Parkinson's disease. It has been discovered that peptides of the invention can be administered independently or can be administered with targeting compounds for targeting to specific brain regions or cells and/or delivery across the blood brain barrier. The administration with targeting compounds may include administration of identified peptides conjugated to one or more targeting compounds, or administration of identified peptides in association with, but not conjugated to, one or more targeting compounds.

According to one aspect of the invention, methods for inhibiting neuronal cell death in a subject are provided. The methods include administering to a subject in need of such treatment a neuroprotective and/or neurorestorative peptide in an amount effective to inhibit neuronal cell death in the subject, wherein the neuroprotective and/or neurorestorative peptide is $Y-Z_N$, wherein Y is a peptide moiety having an amino acid sequence set forth as one of SEQ ID NOs:1-8 or 23, Z is a targeting compound moiety, and N is 0, 1, 2, or 3. In some embodiments, the neuroprotective and/or neurorestorative peptide is a protected peptide. In certain embodiments, Z is attached to the N terminal of Y, the C terminal of Y, or a side chain of Y. In some embodiments, N is 0. In some embodiments, N is 1, 2, or, 3. In some embodiments, the protected peptide is an N or C terminal protected peptide. In certain embodiments, the protected peptide is an N-acetylated peptide. In some embodiments, the protected peptide has one or more stabilized bonds. In some embodiments, the protected peptide includes one or more D-amino acids, a -psi[CH$_2$NH]— reduced amide peptide bond, a -psi[COCH$_2$]— ketomethylene peptide bond, a -psi[CH(CN)NH]— (cyanomethylene)amino peptide bond, a -psi[CH$_2$CH(OH)]— hydroxyethylene peptide bond, a -psi[CH$_2$O]— peptide bond, and/or a -psi[CH$_2$S]— thiomethylene peptide bond. In certain embodiments, the protected peptide includes one or more 1-3 D-amino acids. In some embodiments, the subject has or is suspected of having neuronal cell death associated with Parkinson's disease (PD), Alzheimer's disease, Lewy body disease, stroke, brain injury, spinal cord injury, aging, cardiovascular disease, macular degeneration, toxin exposure, poisoning, Tardive dyskinesia, high altitude sickness, CNS diseases with neuronal degeneration, metabolic disorder, infection, anoxia, or anoxia due to surgery. In some embodiments, the subject is human. In certain embodiments, the subject is an animal model of a neuronal cell death-associated disease or condition. In some embodiments, the neuronal cell death-associated disease or condition is Parkinson's disease (PD), Alzheimer's disease, Lewy body disease, stroke, brain injury, spinal cord injury, aging, cardiovascular disease, macular degeneration, toxin exposure, poisoning, Tardive dyskinesia, high altitude sickness, CNS diseases with neuronal degeneration, metabolic disorder, infection, anoxia, or anoxia due to surgery. In some embodiments, the targeting compound is a compound that facilitates transport of Y into a cell and/or a compound that facilitates transport of Y across the blood-brain barrier into the brain. In some embodiments, the targeting compound is docosohexaenoic acid, lipoic acid, a transferrin receptor binding antibody, cationized albumin, Met-enkephalin, lipoidal forms of dihydropyridine, a cationized antibody, an acetyl group, an acetyl derivative, or a t-butyl acetyl derivative. In certain embodiments, the targeting compound is conjugated to the N-terminal amino acid of Y. In some embodiments, the lipoic acid is l-lipoic acid. In some embodiments, the lipoic acid is d-lipoic acid. In some embodiments, the cell is a neuronal cell. In certain embodiments, the neuronal cell is a dopaminergic cell. In some embodiments, the neuronal cell is a substantia nigra cell. In some embodiments, the neuroprotective and/or neurorestorative peptide is administered prophylactically to the subject. In certain embodiments, the subject is known to have a neuronal cell death-associated disease or condition. In some embodiments, the neuroprotective and/or neurorestorative peptide is administered in combination with one or more additional drug therapies or treatment regimens for treating a neuronal cell death-associated disease or condition. In some embodiments, Y consists of the amino acid sequence set forth as SEQ ID NO:2 and N is 0. In certain embodiments, Y consists of the amino acid sequence SEQ ID NO:2 and N is 1 or 2. In some embodiments, Y consists of the amino acid sequence SEQ ID NO:23 and N is 0. In some embodiments, Y consists of the amino acid sequence SEQ ID NO:23 and N is 1 or 2.

According to another aspect of the invention, methods for treating a neuronal cell death-associated disease or condition are provided. The methods include, administering to a subject in need of such treatment a neuroprotective and/or neurorestorative peptide in an amount effective to treat the disorder in the subject, wherein the neuroprotective and/or neurorestorative peptide is Y—$Z_N$, wherein Y is a peptide moiety that includes an amino acid sequence set forth as one of SEQ ID NOs:1-8 or 23, Z is a targeting compound moiety, and N is 0, 1, 2, or 3. In some embodiments, the neuroprotective and/or neurorestorative peptide is a protected peptide. In certain embodiments, Z is attached to the N terminal of Y, the C terminal of Y, or a side chain of Y. In some embodiments, the protected peptide is an N or C terminal protected peptide. In some embodiments, the protected peptide is an N-acetylated peptide. In certain embodiments, the protected peptide has one or more stabilized bonds. In some embodiments, the protected peptide includes one or more D-amino acids, a -psi[$CH_2NH$]— reduced amide peptide bond, a -psi[$COCH_2$]— ketomethylene peptide bond, a -psi[CH(CN)NH]— (cyanomethylene)amino peptide bond, a -psi[$CH_2CH(OH)$]— hydroxyethylene peptide bond, a -psi[$CH_2O$]— peptide bond, and/or a -psi[$CH_2S$]— thiomethylene peptide bond. In some embodiments, the protected peptide includes one or more 1-3 D-amino acids. In some embodiments, the neuronal cell death-associated disease or condition is Parkinson's disease (PD), Alzheimer's disease, Lewy body disease, stroke, brain injury, spinal cord injury, aging, cardiovascular disease, macular degeneration, toxin exposure, poisoning, Tardive dyskinesia, high altitude sickness, CNS diseases with neuronal degeneration, metabolic disorder, infection, anoxia, or anoxia due to surgery. In certain embodiments, the subject is human. In some embodiments, the subject is an animal model of the neuronal cell death-associated disease or condition. In some embodiments, the neuronal cell death-associated disease or condition is Parkinson's disease (PD), Alzheimer's disease, Lewy body disease, stroke, brain injury, spinal cord injury, aging, cardiovascular disease, macular degeneration, toxin exposure, poisoning, Tardive dyskinesia, high altitude sickness, CNS diseases with neuronal degeneration, metabolic disorder, infection, anoxia, or anoxia due to surgery. In some embodiments, the targeting compound is a compound that facilitates transport of Y into a cell and/or a compound that facilitates transport of Y across the blood-brain barrier into the brain. In certain embodiments, the targeting compound is docosohexaenoic acid, lipoic acid, a transferrin receptor binding antibody, cationized albumin, Met-enkephalin, lipoidal forms of dihydropyridine, a cationized antibody, an acetyl group, an acetyl derivative, or a t-butyl acetyl derivative. In some embodiments, the targeting compound is conjugated to the N-terminal amino acid of Y. In some embodiments, the lipoic acid is l-lipoic acid. In some embodiments, the lipoic acid is d-lipoic acid. In certain embodiments, the cell is a neuronal cell. In some embodiments, the neuronal cell is a dopaminergic cell. In some embodiments, the neuronal cell is a substantia nigra cell. In certain embodiments, the neuroprotective and/or neurorestorative peptide is administered prophylactically to the subject. In some embodiments, the subject is known to have the neuronal cell death-associated disease or condition. In some embodiments, the neuroprotective and/or neurorestorative peptide is administered in combination with one or more additional drug therapies or treatment regimens for treating the neuronal cell death-associated disease or condition. In some embodiments, Y consists of the amino acid sequence set forth as SEQ ID NO:2 and N is 0. In certain embodiments, Y consists of the amino acid sequence SEQ ID NO:2 and N is 1 or 2. In some embodiments, Y consists of the amino acid sequence SEQ ID NO:23 and N is 0. In some embodiments, Y consists of the amino acid sequence SEQ ID NO:23 and N is 1 or 2.

According to yet another aspect of the invention, compositions that include a neuroprotective and/or neurorestorative peptide having a formula Y—$Z_N$, wherein Y is a peptide moiety consisting of a sequence set forth as one of SEQ ID NOs:1-8, or 23, Z is a targeting compound moiety, and N is 1, 2, or 3 are provided. In some embodiments, the neuroprotective and/or neurorestorative peptide is a protected peptide. In certain embodiments, Z is attached to the neuroprotective and/or neurorestorative peptide at the N-terminal, the C terminal, or a side chain of the peptide. In some embodiments, the protected peptide is an N or C terminal protected peptide. In some embodiments, the protected peptide is an N-acetylated peptide. In certain embodiments, the protected peptide has one or more stabilized bonds. In some embodiments, the protected peptide includes one or more D-amino acids, a -psi[$CH_2NH$]— reduced amide peptide bond, a -psi[$COCH_2$]— ketomethylene peptide bond, a -psi[CH(CN)NH]— (cyanomethylene)amino peptide bond, a -psi[$CH_2CH(OH)$]— hydroxyethylene peptide bond, a -psi[$CH_2O$]— peptide bond, and/or a -psi[$CH_2S$]— thiomethylene peptide bond. In some embodiments, the protected peptide comprises one or more 1-3 D-amino acids. In certain embodiments, the targeting compound is a compound that facilitates transport of Y into a cell and/or a compound that facilitates transport of Y across the blood-brain barrier. In some embodiments, the targeting compound is docosohexaenoic acid, lipoic acid, a transferrin receptor binding antibody, cationized albumin, Met-enkephalin, lipoidal forms of dihydropyridine, a cationized antibody, an acetyl group, an acetyl derivative, or a t-butyl acetyl derivative. In some embodiments, the targeting compound is conjugated to the N-terminal amino acid of Y. In some embodiments, the lipoic acid is l-lipoic acid. In certain embodiments, the lipoic acid is d-lipoic acid. In some embodiments, the cell is a neuronal cell. In some embodiments, the neuronal cell is a dopaminergic cell. In some embodiments, the neuronal cell is a substantia nigra cell. In certain embodiments, the composition also includes a pharmaceutically acceptable carrier. In some embodiments, Y consists of the amino acid sequence SEQ ID NO:2 and N is 1 or 2. In some embodiments, Y consists of the amino acid sequence SEQ ID NO:23 and N is 1 or 2.

According to another aspect of the invention, isolated expression vector are provided. The isolated expression vectors include an isolated nucleic acid that encodes a peptide wherein the amino acid sequence of the peptide consists of a sequence set forth as one of SEQ ID NOs:1-8, or 23.

According to yet another aspect of the invention, pharmaceutical preparations are provided that include any isolated expression vector of any of the foregoing aspects of the invention.

According to yet another aspect of the invention, kits for inhibiting neuronal cell death in a cell, tissue, and/or subject in accordance with the any of the methods and embodiments of the foregoing aspects of the invention are provided. The kits may include, a package housing a first container containing at least one dose of a neuroprotective and/or neurorestorative peptide, wherein the neuroprotective and/or neurorestorative peptide is Y—$Z_N$, wherein Y is a peptide moiety consisting of an amino acid sequence set forth as one of SEQ ID NOs:1-8, or 23, Z is either nothing or a targeting compound moiety, and N is 0, 1, 2, or 3, and may include instructions' for using the neuroprotective and/or neurorestorative peptide for inhibiting neuronal cell death in a cell, tissue, and/or subject in need of such treatment. In certain embodiments, N=0. In some embodiments, N=1, 2, or 3. In some embodiments, Z is attached to the N terminal of Y, the C terminal of Y, a side chain of Y, or at another substitutable position on Y. In certain embodiments, the kits may also include a second container containing a compound that is a targeting compound, and instructions for conjugating the targeting compound to the neuroprotective and/or neurorestorative peptide. In some embodiments, the tissue or subject has or is suspected of having neuronal cell death associated with Parkinson's disease (PD), Alzheimer's disease, Lewy body disease, stroke, brain injury, spinal cord injury, aging, cardiovascular disease, macular degeneration, toxin exposure, poisoning, Tardive dyskinesia, high altitude sickness, CNS diseases with neuronal degeneration, metabolic disorder, infection, anoxia, or anoxia due to surgery. In some embodiments, the subject is human. In some embodiments, the subject is an animal model of a neuronal cell death-associated disease or condition. In certain embodiments, the neuronal cell death-associated disease or condition is Parkinson's disease (PD), Alzheimer's disease, Lewy body disease, stroke, brain injury, spinal cord injury, aging, cardiovascular disease, to macular degeneration, toxin exposure, poisoning, Tardive dyskinesia, high altitude sickness, CNS diseases with neuronal degeneration, metabolic disorder, infection, anoxia, or anoxia due to surgery. In some embodiments, the targeting compound is a compound that facilitates transport of Y into a cell and/or facilitates transport of Y across the blood-brain barrier into the brain. In some embodiments, the targeting compound is docosohexaenoic acid, lipoic acid, a transferrin receptor binding antibody, cationized albumin, Met-enkephalin, lipoidal forms of dihydropyridine, a cationized antibody, an acetyl group, an acetyl derivative, or a t-butyl acetyl derivative. In certain embodiments, the lipoic acid is l-lipoic acid. In some embodiments, the lipoic acid is d-lipoic acid. In some embodiments, the cell is a neuronal cell. In certain embodiments, the neuronal cell is a dopaminergic cell. In some embodiments, the neuronal cell is a substantia nigra cell. In some embodiments, the neuroprotective and/or neurorestorative peptide is administered to a subject prophylactically for a neuronal cell death-associated disease or condition. In some embodiments, the neuroprotective and/or neurorestorative peptide is administered to a subject known to have a neuronal cell death-associated disease or condition. In certain embodiments, the neuroprotective and/or neurorestorative peptide is administered in combination with an additional drug for treating a neuronal cell death-associated disease or condition. In some embodiments, the neuroprotective and/or neurorestorative peptide consisting of the amino acid sequence set forth as one of SEQ ID NOs:1-8, or 23 is a protected peptide. In some embodiments, the protected peptide is an N or C terminal protected peptide. In certain embodiments, the protected peptide is an N-acetylated peptide. In some embodiments, the protected peptide has one or more stabilized bonds. In some embodiments, the protected peptide includes one or more D-amino acids, a -psi[$CH_2NH$]— reduced amide peptide bond, a -psi[$COCH_2$]— ketomethylene peptide bond, a -psi[CH(CN)NH]— (cyanomethylene)amino peptide bond, a -psi[$CH_2CH(OH)$]— hydroxyethylene peptide bond, a -psi[$CH_2O$]— peptide bond, and/or a -psi[$CH_2S$]— thiomethylene peptide bond. In certain embodiments, the protected peptide includes one or more 1-3 D-amino acids. In some embodiments, Y consists of the amino acid sequence set forth as SEQ ID NO:2 and N is 0. In some embodiments, Y consists of the amino acid sequence set forth as SEQ ID NO:2 and N is 1 or 2. In some embodiments, Y consists of the amino acid sequence SEQ ID NO:23 and N is 0. In certain embodiments, Y consists of the amino acid sequence SEQ ID NO:23 and N is 1 or 2.

According to yet another aspect of the invention, pharmaceutical compositions are provided. The pharmaceutical compositions include a neuroprotective and/or neurorestorative peptide of the general formula Y—$Z_N$, wherein Y is a peptide moiety consisting of an amino acid sequence set forth as one of SEQ ID NOs:1-8, or 23, Z is either nothing or a targeting compound moiety, and N is 0, 1, 2, or 3; and a pharmaceutically acceptable carrier. In some embodiments, Z is attached to the N terminal of Y, the C terminal of Y, or a side chain of Y. In some embodiments, the neuroprotective and/or neurorestorative peptide is a protected peptide. In some embodiments, the protected peptide is an N or C terminal protected peptide. In certain embodiments, the protected peptide is an N-acetylated peptide. In some embodiments, wherein the protected peptide has one or more stabilized bonds. In some embodiments, the protected peptide includes one or more D-amino acids, a -psi[$CH_2NH$]— reduced amide peptide bond, a -psi[$COCH_2$]— ketomethylene peptide bond, a -psi[CH(CN)NH]—(cyanomethylene)amino peptide bond, a -psi[$CH_2CH(OH)$]— hydroxyethylene peptide bond, a -psi[$CH_2O$]— peptide bond, and/or a -psi[$CH_2S$]— thiomethylene peptide bond. In some embodiments, the protected peptide includes one or more 1-3 D-amino acids. In certain embodiments, the targeting compound is a compound that facilitates transport of Y into a cell and/or facilitates transport of Y across the blood-brain barrier into the brain. In some embodiments, the targeting compound is docosohexaenoic acid, lipoic acid, a transferrin receptor binding antibody, cationized albumin, Met-enkephalin, lipoidal forms of dihydropyridine, a cationized antibody, an acetyl group, an acetyl derivative, or a t-butyl acetyl derivative. In some embodiments, the targeting compound is lipoic acid. In certain embodiments, the lipoic acid is l-lipoic acid. In some embodiments, the lipoic acid is d-lipoic acid. In some embodiments, the cell is a neuronal cell. In certain embodiments, the neuronal cell is a dopaminergic cell. In some embodiments, the neuronal cell is a substantia nigra cell. In some embodiments, the neuroprotective and/or neurorestorative peptide is administered to a subject prophylactically for a neuronal cell death-associated disease or condition. In certain embodiments, the neuroprotective and/or neurorestorative peptide is administered to a subject known to have a neuronal cell death-associated disease or condition. In some embodiments, the neuroprotective and/or neurorestorative peptide is administered in combination with one or more additional drug therapies or treatment regimens for treating a neuronal cell death-associated disease or condition. In some embodiments, the neuronal cell death-associated disease or condition is Parkinson's disease (PD), Alzheimer's disease, Lewy body disease, stroke, brain injury, spinal cord injury, aging, cardiovascular disease, macular degeneration, toxin exposure, poisoning, Tardive dyskinesia, high altitude sickness, CNS diseases with to neuronal degeneration, metabolic disorder, infection, anoxia, or anoxia due to surgery. In certain embodiments, Y consists of the amino acid sequence set forth as SEQ ID NO:2 and N is 0. In some embodiments, Y consists of the amino acid sequence set forth as SEQ ID NO:2 and N is 1, 2, or 3. In certain embodiments, Y consists of the amino acid sequence SEQ ID NO:23 and N is 0. In some embodiments, Y consists of the amino acid sequence SEQ ID NO:23 and N is 1 or 2.

In certain embodiments of any of the aforementioned aspects of the invention, the neuroprotective and/or neurorestorative peptide is administered in combination with one or more additional drug therapies or treatment regimens for treating the neuronal cell death-associated disease or condition. In some embodiments of any of the aforementioned aspects of the invention, the neuroprotective and/or neurorestorative peptide is linked to a detectable moiety.

In yet another aspect of the invention, a neuroprotective and/or neurorestorative peptide may be administered in combination with a compound that increases transport across the blood-brain barrier (BBB), wherein the neuroprotective and/or neurorestorative peptide is associated with, or conjugated to the compound. In some embodiments, the compound that increases transport across the BBB increases permeability of the BBB. In some embodiments, the permeability is increased transiently. In some embodiments, co-administration of a neuroprotective and/or neurorestorative peptide permits the peptide to cross a permeabilized BBB.

In yet another aspect of the invention, a neuroprotective and/or neurorestorative peptide of the invention is linked to a detectable moiety. In some embodiments, the detectable moiety may be biotin, a fluorophore, chromophore, enzymatic or a radioactive moiety. In some embodiments, the detectably labeled neuroprotective and/or neurorestorative peptide may be detected in vivo or in vitro. In some embodiments, the labeled neuroprotective and/or neurorestorative peptide may be detected as a determination of the location of neuronal cell death.

In yet another aspect of the invention, a neuroprotective and/or neurorestorative peptide is contacted with cells in culture to reduce cell death in culture.

According to another aspect of the invention, isolated expression vectors are provided. The isolated expression vectors include a nucleic acid that encodes a peptide wherein the amino acid sequence of the peptide consists of a sequence set forth as one of SEQ ID NOs:1-19, 23, or 25-74.

According to yet another aspect of the invention a pharmaceutical preparation that includes the foregoing isolated expression vector is provided.

Neurorestorative and/or neuroprotective peptides set forth herein as SEQ ID NOs:1-74 may be used in the foregoing aspects of the invention. Lipoic acid, or other targeting compound, may be conjugated to or administered with any of the peptides set forth as SEQ ID NO:1-19, 23, and 25-74 and used in any of the foregoing aspects and embodiments of the invention. Neurorestorative and/or neuroprotective peptides set forth as SEQ ID NOs:1-74, protected or unprotected, may be used in any of the foregoing aspects and/or embodiments of the invention. In any of the foregoing aspects and embodiments of the invention, lipoic acid, which is administered to a cell, tissue, or subject may provide anti-inflammatory effects to the cell, tissue, or subject. Administration of lipoic acid either conjugated to or administered with a neurorestorative and/or neuroprotective peptide set forth as SEQ ID NO:1-19, 23 and 25-74, may be useful to augment neuroprotective and/or neurorestorative effects of the peptides in any of the foregoing methods or aspects of the invention. In some aspects of the invention, one, two, or more additional amino acids may be added to one and/or both ends of a peptide provided herein, such that the peptide retains a neuroprotective and/or neurorestorative function of a peptide of the invention. Such functional alternative peptide sequences may be used in the methods and compositions of the invention In some aspects, the invention includes the use of the foregoing compositions in the preparation of a medicament, particularly a medicament for prevention and/or treatment of a neurological disease or condition associated with neuronal cell death, such as PD.

These and other objects of the invention will be described in further detail in connection with the detailed description of the invention.

DETAILED DESCRIPTION OF THE INVENTION

Figure 1:
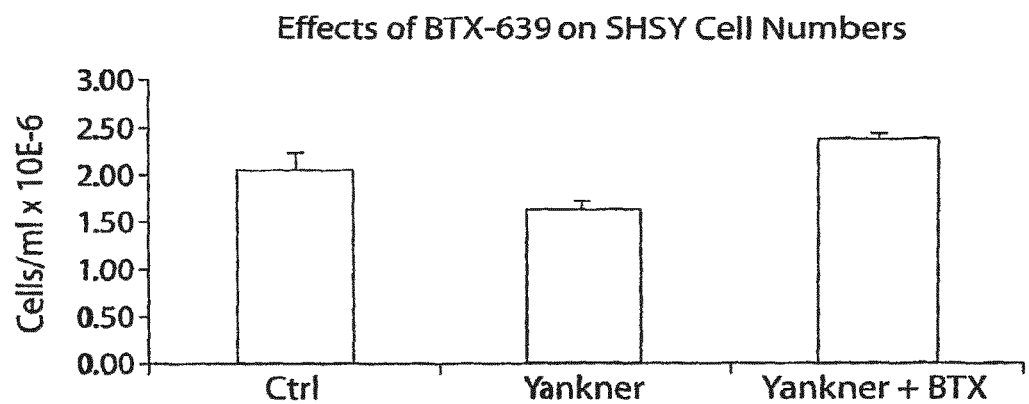
FIG. 1. is a histogram demonstrating the effect of BTX0-639 [peptide DQ (SEQ ID NO:2)] on SHSY cell numbers. Each histobar represents the mean of four independent measures. Error bars denote one standard deviation. The following p values were obtained using a two-tailed student's t-test: Ctrl vs Yankner 0.005; Yankner vs Yankner+BTX 0.006; Ctrl vs Yankner+BTX 0.03. BTX=peptide DQ (SEQ ID NO:2), ctrl=control.

The invention involves, in some aspects, peptides that inhibit neuronal cell death. Additionally, methods of the invention, in part, involve the administration of the peptides to reduce or inhibit neuronal cell death in subjects with, or at risk of developing, a neuronal cell death-associated disease and/or condition. As used herein, neuronal cell death-associated diseases or conditions include, but are not limited to, Parkinson's disease, Alzheimer's disease, Lewy body disease, stroke, brain injury, aging, cardiovascular disease, macular degeneration, toxicity, poisoning, Tardive dyskinesia, high altitude sickness, CNS diseases with neuronal degeneration, anoxia, metabolic disorder, infection, etc. In each neuronal cell death-associated disease or condition, an increase neuronal cell death, relative to a disease-free and/or condition-free circumstance, is characteristic of the disease or condition. For example, in PD, the loss of neurons in the substantia nigra pars compacta has been identified as a characteristic of the disease. Additionally, neuronal cell death is a known characteristic of Alzheimer's disease and brain injury. One of ordinary skill in the art will be able to determine and recognize additional diseases and conditions that are associated with neuronal cell death to which the methods of the invention can be applied. In some embodiments the neuronal cell death-associated disease and/or conditions involves cell death in the peripheral nervous system. The methods of the invention may be useful to reduce cell death associated with the peripheral nervous system as well as in the central nervous system.

Compositions of the invention include, in part, neuroprotective and/or neurorestorative peptides, three of which are set forth as EVDDDQ (SEQ ID NO:1), AA (SEQ ID NO:23), and DQ (SEQ ID NO:2). SEQ ID NOs:1, 2, and 23, and amino acid sequences of some additional exemplary neuroprotective and/or neurorestorative peptides of the invention are set forth in Table 1.

TABLE 1

Amino acid sequences of neuroprotective and/or neurorestorative peptides

| $X_1$ | $X_2$ | $X_3$ | $X_4$ | $X_5$ | $X_6$ | Sequence ID Number |
|---|---|---|---|---|---|---|
| E | V | D | D | D | Q | (SEQ ID NO: 1) |
| D | Q | — | — | — | — | (SEQ ID NO: 2) |
| Q | D | D | D | V | E | (SEQ ID NO: 3) |
| V | F | T | P | P | S | (SEQ ID NO: 4) |
| D | D | V | E | — | — | (SEQ ID NO: 5) |
| R | F | Q | L | — | — | (SEQ ID NO: 6) |
| Q | L | D | D | V | E | (SEQ ID NO: 7) |
| R | F | Q | L | T | E | (SEQ ID NO: 8) |
| — | — | D | D | D | Q | (SEQ ID NO: 9) |
| E | V | D | D | — | — | (SEQ ID NO: 10) |
| E | V | — | — | — | — | (SEQ ID NO: 11) |
| — | V | D | D | D | Q | (SEQ ID NO: 12) |
| E | V | D | D | D | — | (SEQ ID NO: 13) |
| — | — | — | D | D | Q | (SEQ ID NO: 14) |
| E | V | D | — | — | — | (SEQ ID NO: 15) |
| — | V | D | D | D | — | (SEQ ID NO: 16) |
| — | V | D | D | — | — | (SEQ ID NO: 17) |
| — | V | D | — | — | — | (SEQ ID NO: 18) |
| — | — | D | D | — | — | (SEQ ID NO: 19) |
| [Lip]-V | F | T | P | P | S | (SEQ ID NO: 20) |
| [Ac]-Q | D | D | D | V | E | (SEQ ID NO: 21) |
| [Lip]-E | V | D | D | D | Q | (SEQ ID NO: 22) |
| A | A | — | — | — | — | (SEQ ID NO: 23) |
| — | — | — | [Lip]- | D | Q | (SEQ ID NO: 24) |
| Q | D | — | — | — | — | (SEQ ID NO: 25) |
| Q | D | D | — | — | — | (SEQ ID NO: 26) |
| — | D | D | D | — | — | (SEQ ID NO: 27) |
| — | — | D | D | V | E | (SEQ ID NO: 28) |
| — | — | — | D | V | E | (SEQ ID NO: 29) |
| — | D | D | D | V | — | (SEQ ID NO: 30) |
| — | D | D | D | V | E | (SEQ ID NO: 31) |
| Q | D | D | D | — | — | (SEQ ID NO: 32) |
| Q | D | D | D | V | — | (SEQ ID NO: 33) |
| — | — | — | D | V | — | (SEQ ID NO: 34) |
| V | F | — | — | — | — | (SEQ ID NO: 35) |
| V | F | T | — | — | — | (SEQ ID NO: 36) |
| V | F | T | P | — | — | (SEQ ID NO: 37) |
| V | F | T | P | P | — | (SEQ ID NO: 38) |
| — | F | T | P | P | S | (SEQ ID NO: 39) |
| — | F | T | P | P | — | (SEQ ID NO: 40) |
| — | F | T | P | — | — | (SEQ ID NO: 41) |
| — | F | T | — | — | — | (SEQ ID NO: 42) |
| — | — | T | P | P | S | (SEQ ID NO: 43) |
| — | — | T | P | P | — | (SEQ ID NO: 44) |
| — | — | T | P | — | — | (SEQ ID NO: 45) |
| — | — | — | P | P | S | (SEQ ID NO: 46) |
| — | — | — | P | P | — | (SEQ ID NO: 47) |
| — | — | — | — | P | S | (SEQ ID NO: 48) |
| R | F | Q | — | — | — | (SEQ ID NO: 49) |
| — | F | Q | L | — | — | (SEQ ID NO: 50) |
| — | F | Q | — | — | — | (SEQ ID NO: 51) |
| — | — | Q | L | — | — | (SEQ ID NO: 52) |
| Q | L | D | D | V | — | (SEQ ID NO: 53) |
| Q | L | D | D | — | — | (SEQ ID NO: 54) |
| Q | L | D | — | — | — | (SEQ ID NO: 55) |
| Q | L | — | — | — | — | (SEQ ID NO: 56) |
| — | L | D | D | V | E | (SEQ ID NO: 57) |
| — | L | D | D | V | — | (SEQ ID NO: 58) |
| — | L | D | D | — | — | (SEQ ID NO: 59) |
| — | L | D | — | — | — | (SEQ ID NO: 60) |
| — | — | D | D | V | E | (SEQ ID NO: 61) |

TABLE 1-continued

Amino acid sequences of neuroprotective and/or neurorestorative peptides

| $X_1$ | $X_2$ | $X_3$ | $X_4$ | $X_5$ | $X_6$ | Sequence ID Number |
|---|---|---|---|---|---|---|
| – | – | D | D | V | – | (SEQ ID NO: 62) |
| – | – | D | D | – | – | (SEQ ID NO: 63) |
| – | – | – | D | V | E | (SEQ ID NO: 64) |
| – | – | – | D | V | – | (SEQ ID NO: 65) |
| – | – | – | – | V | E | (SEQ ID NO: 66) |
| R | F | Q | L | T | – | (SEQ ID NO: 67) |
| – | F | Q | L | T | E | (SEQ ID NO: 68) |
| – | F | Q | L | T | – | (SEQ ID NO: 69) |
| – | – | Q | L | T | E | (SEQ ID NO: 70) |
| – | – | Q | L | T | – | (SEQ ID NO: 71) |
| – | – | – | L | T | E | (SEQ ID NO: 72) |
| – | – | – | L | T | – | (SEQ ID NO: 73) |
| – | – | – | – | T | E | (SEQ ID NO: 74) |

Neuroprotective and/or neurorestorative peptides of the invention may also include peptides that have an overall sequence set forth as $X_1X_2X_3X_4X_5X_6$ but have alternative amino acid residues than those of the peptide set forth as SEQ ID NO:1. Some alternative sequences of neuroprotective and/or neurorestorative peptides of the invention are provided in Table 1. Note that some sequences are the same but arise as fragments of different longer peptides, for example, SEQ ID NOs:28, 29, and 34 are the same as SEQ ID NOs:61, 64, and 65, respectively.

Neuroprotective and/or neurorestorative peptides of the invention reduce death of neuronal cells induced by a neuronal cell death-associated disease or condition when the cells are contacted with the neuroprotective and/or neurorestorative peptide. Thus, as used herein, the term "neuroprotective and/or neurorestorative peptide" means a peptide that when contacted with a cell, tissue, and/or subject can reduce the amount of neuronal cell death in the cell, tissue, and/or subject compared to a control amount of cell death (e.g., in a cell, tissue and/or subject that has the neuronal cell death-associated disease or condition but is not contacted with the peptide, etc.). Neuroprotective and/or neurorestorative peptides of the invention include, but are not limited to, a peptide with an amino acid sequence set forth as one of SEQ ID NOs:1-8, or 23, protected or unprotected, wherein the peptide reduces or inhibits neuronal cell death associated with a disease and/or condition.

In some embodiments, SEQ ID NOs:1-8, and 23, are natural peptides, e.g., the bonds are natural peptide bonds and the amino acids are natural amino acids. The invention also includes in some aspects, neuroprotective and/or neurorestorative peptides that are protected peptides having an amino acid sequence set forth as one of SEQ ID NOs:1-8, or 23. Examples of protected peptides that have an amino acid sequence set forth as one of SEQ TA) NOs:1-8, or 23, although not intended to be limiting, are peptides with the sequence of one of SEQ ID NOs:1-8, or 23 in which the terminal amino group is N-acetylated. Neuroprotective and/or neurorestorative peptides of the invention can be administered alone (e.g., with no targeting compound), or administered with or conjugated to a compound that facilitates delivery of the peptide across the blood-brain barrier or delivery to and/or entry into a specific cell type.

As used herein the term "neuroprotective" means protection of a neuron from cell death. A peptide that is neuroprotective is a peptide that when contacted with a cell, tissue, or subject, protects the cell, tissue, and/or subject from an event or condition that would normally result in neuronal cell death (e.g., can prevent or reduce the likelihood of cell death). It will be understood that a neuroprotective peptide of the invention need not eliminate all neuronal cell death, but rather may reduce the amount of cell death as compared to a control amount of neuronal cell death. A neuroprotective peptide of the invention may reduce neuronal cell death by at least 1, 2, 3, 4, 5, 6, 7, 8, 9, 10, 15, 20, 25, 30, 35, 40, 50, 60, 70, 80, 90, or 100% (including all percentages in between) as compared to a control amount of neuronal cell death. A reduction in the amount of neuronal cell death may be evidenced by the restoration of function of cells or tissues, and/or regain of neuronal function in a subject.

An example of a neuroprotective function of a peptide of the invention, although not intended to be limiting, is the protection from loss of neuronal cells and/or tissues when the cells and/or tissues are contacted with the peptide in advance or coincident with an injury or to a genetically generated insult event (e.g., biochemical or physical trauma, etc) to the neuronal cells and/or tissues. Thus, the neuroprotective peptide may protect cells from the insult or trauma to neuronal cells and tissues thereby reducing or inhibiting the amount of neuronal cell death in the injured or insulted cells or tissue (e.g., as compared to a control amount).

As used herein, the term "neurorestorative" means restoring or rescuing a cell, tissue, or subject from the effect of an insult, event, or condition that would normally result in neuronal cell death. For example, contacting a neurorestorative peptide of the invention with a cell or a tissue or administering a neurorestorative peptide to a subject who has experienced an event or condition that can result in neuronal cell death may result in restoration of cells and/or tissue function. In some embodiments, a neurorestorative peptide of the invention can be contacted with an injured neuronal cell and can inhibit death and rescue the cell. It will be understood that the restoration of cells (which may be evidenced by the restoration of function of cells or tissues or regain of neuronal function in a subject) need not be to 100% of the original number of cells or amount of cell or tissue function. Rather an increase of at least 1, 2, 3, 4, 5, 6, 7, 8, 9, 10, 15, 20, 25, 30, 35, 40, 50, 60, 70, 80, 90, or 100% (including all percentages in between) in the number and/or function of cells may result from contact with a neurorestorative peptide of the invention.

An example of a neurorestorative function of a peptide, although not intended to be limiting, is the restoration of function of neuronal tissues when contacted with the peptide after an injury or insult event (e.g., biochemical or physical trauma, etc). Thus, an insult or trauma may occur in a neuronal region and the post-injury contact with a neurorestorative peptide of the invention may reduce or inhibit the amount of cell death in the brain region.

A neuroprotective and/or neurorestorative peptide of the invention can be used in the methods of the invention to reduce the amount of neuronal cell death and for the prevention and/or treatment of a neuronal cell death-associated condition in cells, tissues, and subjects. Methods of the invention involve the administration of neuroprotective and/or neurorestorative peptides and therefore are useful to reduce or prevent diseases and/or conditions associated with neuronal cell death. As used herein, the term "neurological diseases and conditions associated with neuronal cell death" includes, but is not limited to Parkinson's disease (PD), Alzheimer's disease, Lewy body disease, stroke, brain injury, spinal cord injury, aging, cardiovascular disease, macular degeneration, toxin exposure, poisoning, Tardive dyskinesia, high altitude sickness, CNS diseases with neuronal degeneration, metabolic disorder, infection, anoxia, anoxia due to surgery, etc. It will be understood that neuronal cell death that is associated with an event, disease or condition may be a direct result of the event, disease, or condition or may result indirectly from the event, disease, or condition. Thus some neuronal cell death may be a downstream result of an event, disease, or condition.

As used herein, the term "subject" means any mammal that may be in need of treatment with a neuroprotective and/or neurorestorative peptide of the invention to reduce neuronal cell death. As used herein the phrase "subject in need of such treatment" means a subject who is known to have, or is considered to be at risk of having, a disease or condition associated with neuronal cell death. Subjects include but are not limited to: humans, non-human primates, cats, dogs, sheep, pigs, horses, cows, rodents such as mice, rats, hamsters, gerbils, etc. In some aspects of the invention, a subject is known to have, or is considered to be at risk of having, a disease or condition associated with neuronal cell death. In some embodiments, a subject is a mammal that is an animal model for a neuronal cell death-associated disease or condition. One of ordinary skill in the art will recognize that animal models of a neuronal cell death-associated disease or condition (e.g., see Examples) may be generated by genetic engineering or by chemical or physical treatment (e.g., stroke models, PD models, etc.).

In some embodiments, cells outside of a subject may be contacted with a neurorestorative and/or neuroprotective peptide of the invention. For example, cells in culture. The neuroprotective and/or neurorestorative peptides of the invention may be useful to protect cells (e.g., cells in culture) from cell death. Examples of cells in culture that may be contacted with a neuroprotective and/or neurorestorative peptide include cells known to be afflicted with a neuronal cell death-associated disease or condition (e.g., AD, or Parkinson's disease, etc). In some embodiments, the cells (e.g., cultured cells) may not be afflicted with a disease or condition associated with neuronal cell death, but may be contacted with a neuroprotective and/or neurorestorative peptide to help reduce cell death and to maintain living cells in culture. In some embodiments the cell and/or tissue that is contacted with a neuroprotective and/or neurorestorative peptide of the invention is contacted in vivo, e.g., in a subject.

The methods and compositions of the invention can be used for prophylactic treatment and/or for active treatment of a cell, tissue, and/or subject. As used herein, "active" treatment means treatment of a cell, tissue, or subject known to have a neuronal cell death-associated disease or condition. As used herein "prophylactic" treatment is treatment before a subject is confirmed to have a disease or condition, e.g., it is administering a neuroprotective and/or neurorestorative peptide of the invention in advance of a tissue or subject having an insult or injury that results in neuronal cell death—e.g., a neuronal cell death-associated disease or condition. Prophylactic treatment may be administered to a subject "at risk" or "at elevated risk" of having or likely to have a neuronal cell death-associated disease or condition.

As used herein, a subject "at risk" is a subject who is considered more likely to develop a disease state or a physiological state than a subject who is not at risk. A subject's level of risk of a disease or condition associated with neuronal cell death may be considered to be an "elevated" risk, which means the subject is at a higher than normal risk of the disease or condition. A subject "at risk" or at "elevated risk" may or may not have detectable symptoms indicative of the disease or physiological condition, and may or may not have displayed detectable disease prior to the treatment methods (e.g., therapeutic intervention) described herein. "At risk" denotes that a subject has one or more so-called risk factors. A subject having one or more of these risk factors has a higher probability of developing one or more disease(s) or physiological condition(s) than a subject without some or all of these risk factor(s). Generally, risk factors can include, but are not limited to, history of family members developing one or more diseases (e.g., Parkinson's disease, Alzheimer's disease, high altitude sickness, stroke, cardiovascular disease, macular degeneration, Tardive Dyskinesia, CNS diseases with neuronal degeneration, etc), related conditions, or pathologies, history of previous disease, age, gender, race, diet, presence of precursor disease, genetic (i.e., hereditary) considerations, and environmental exposure or accident. It will be understood that one of skill in the medical arts (e.g., health-care practitioners, etc) may assess a combination of possible risk factors to determine whether a subject is at increased risk for a disease or condition.

It will be understood that the assessment of a subject's risk may be based on primary risk factors such as family history, genetic profile, etc. in light of secondary risk factors such as age or gender. Risk factors will differ for different neuronal cell death-associated diseases and conditions. For example, risk factors for AD or Parkinson's disease may be family history or the existence of a genetic predisposition, age, etc. Examples of risk factors for high altitude sickness may be a previous incidence of high altitude sickness, an upcoming high altitude exposure, age, etc. One of ordinary skill in the art will recognize the parameters for consideration of specific risk factors for different diseases and/or conditions.

The level of risk can be assessed using standard methods known to those in the art. For example, based on factors such as genetic analysis, medical history, family medical history, and current medical condition, a health-care professional may assess a percentage chance that a subject will have or will develop a disease or condition associated with neuronal cell death (e.g., PD or AD, etc.)., For example, a health-care professional may determine that a subject with a family history of PD has a greater chance of developing PD than a person with no family history of PD. Thus, the subject has an elevated risk of having the condition. Those of skill in the art will recognize that a subject's level of risk for neuronal cell death-associated diseases or conditions can also be evaluated using additional methods such as those described elsewhere herein. Another example of a subject at risk or elevated risk for a disease or condition associated with neuronal cell death may be a subject who has experienced a stroke and/or a subject who experiences a neurological injury (e.g., a head injury or trauma) and therefore is now at elevated risk for continuing damage or injury to the brain and/or spinal cord. Another example of subject at elevated risk for neuronal cell death may be a subject who is above an age cut-off; for example a subject who is over 40, 45, 50, 55, 60, 65, 70, 75, 80, 85, 90, or more years of age.

Methods of the invention include administration of a neuroprotective and/or neurorestorative peptide of the invention that preferentially targets neuronal cells and/or tissues. Although not wishing to be bound by a particular theory, neuroprotective and/or neurorestorative peptides of the invention are believed to target cells that have oxygen deprivation-associated damage, and thus may target cells associated with a neuronal cell death-associated disease or condition, such as those described herein. Thus, neuroprotective and/or neurorestorative peptides of the invention may directly and independently target neurons that have oxygen deprivation-associated damage. Although not wishing to be bound by a particular theory, neuroprotective and/or neurorestorative peptides of the invention may act on Protein Kinase C to inhibit the generation of its catalytic subunit PKC-delta or may work as inhibitors of the phosphorylation step of transcription factor Bcl-2, thereby blocking the generation of Caspases thus preventing or mitigating neuronal death.

In some embodiments of the invention, neuroprotective and/or neurorestorative peptides of the invention may be administered not in association with or conjugated to a targeting compound. Such "independent" neuroprotective and/or neurorestorative peptides of may be used in the methods and kits of the invention. Neuroprotective and/or neurorestorative peptides of the invention that are capable of crossing the blood brain barrier without a targeting compound can be administered peripherally and will enter the brain and function as neuroprotective and/or neurorestorative peptides. A non-limiting example is DQ (SEQ ID NO:2), which can be peripherally administered (e.g., orally etc.) and will cross the BBB and enter neuronal cells and function as a neuroprotective and/or neurorestorative peptide without conjugation to or administration with an additional transport compound. In certain embodiments of the invention, neuroprotective and/or neurorestorative peptides of the invention may be administered in association with or conjugated to a targeting compound. A non-limiting example is [Lip]-DQ (SEQ ID NO:24), which can be peripherally administered and will cross the BBB and enter neuronal cells and function as a neuroprotective and/or neurorestorative peptide.

In addition to independent administration and targeting in the absence of a targeting compound, neuroprotective and/or neurorestorative peptides of the invention can also be specifically targeted to neuronal cells and tissues using various delivery methods, including, but not limited to: administration to neuronal tissue, the addition of targeting compounds to preferentially direct the compounds of the invention to neuronal tissues, etc. As used herein the term "preferentially direct" means to increase delivery of a neuroprotective and/or neurorestorative peptide of the invention to and/or into a specific target cell type or target tissue type as compared to delivery of a neuroprotective and/or neurorestorative peptide to a non-targeted cell and/or tissue.

Methods of the invention to target and deliver a neuroprotective and/or neurorestorative peptide of the invention to a neuronal tissue also may include the use of a targeting compound that delivers a neuroprotective and/or neurorestorative peptide of the invention across the blood brain barrier. Methods and compositions of the invention for delivery across the blood brain barrier include the use of a targeting compound such as fatty acids, fatty amines, fatty alcohols, etc. that are covalently linked to a neuroprotective and/or neurorestorative peptide of the invention using standard methods. Additional methods to specifically target peptides and compositions of the invention to brain tissue are known to those of ordinary skill in the art.

The neuroprotective and/or neurorestorative peptides of the invention may be isolated peptides. As used herein, "isolated" means a peptide in a circumstance that does not occur in nature, for example, because the peptide is modified from a naturally occurring peptide (e.g., by alteration of one or more amino acids), because the peptide is attached to a molecule that is not a peptide or because the peptide does not contain the flanking amino acids that are present in nature. It will be understood that an isolated peptide may be conjugated to other compounds and/or molecules, including peptides, for use in the invention. For example, a neuroprotective and/or neurorestorative peptide of the invention may have the general formula: $Y-Z_N$ with Y is a moiety of a peptide (e.g., consisting of an amino acid sequence such as one set forth as SEQ ID NOs:1-19, 23, or 25-74), Z is a moiety of a targeting compound, and N is 0, 1, 2, or 3. As used herein, a targeting compound may be a compound that facilitates transport of Y to and/or into a cell and/or facilitates transport of Y across the blood brain barrier. In such an embodiment, the neuroprotective and/or neurorestorative peptide is an isolated peptide, even if Z is a peptide that is conjugated to Y, as long as Z is not the contiguous amino acids that are present flanking the amino acid sequence of Y in nature. It will be understood that as referred to herein, Y and Z, when conjugated, are moieties of Y and Z. Thus, when a peptide (Y) is conjugated to a targeting compound (Z), Y is a peptide moiety and Z is a targeting compound moiety. For example, Z is a moiety of a targeting agent when conjugated to Y, which entailed the adjustment of Z such as the loss of a hydrogen, OH group, or other atom(s), permitting its conjugation to Y. Similarly, Y is a moiety of a peptide when conjugated to Z, for which Y has been adjusted by the loss of a hydrogen or other atom(s) for conjugation to Z. As is recognized by those of ordinary skill in the art, a moiety of an amino acid is formed when a reactive group on the amino acid is reacted with a targeting compound to form a covalent bond such as a amide bond, ester bond, etc. As a non-limiting example, the carboxylic acid group of a lipoic acid and an amine group of a peptide may be coupled to form an amide group, with the resulting conjugate including a lipoic acid moiety and a peptide moiety.

It will be understood by those of skill in the art that the representation of a neuroprotective and/or neurorestorative peptide as $Y-Z_N$ wherein N can be 0, 1, 2, or 3 is intended to indicate that 0, 1, 2, or 3 targeting compounds may be attached to (e.g., conjugated to) Y. Thus, when N is zero, there is no targeting compound attached to Y. It will be understood that if N is more than one, the targeting compounds may be, but need not be, all of the same type or may be two or more different types of transport compounds. There may be one, two or three different targeting compounds attached to Y. In some embodiments of the invention, up to 4, 5, 6 or more targeting compounds may be conjugated to a neurorestorative and/or neuroprotective peptide of the invention as long as the neuroprotective and/or neurorestorative function of the peptide is retained.

The representation $Y-Z_N$ is not intended as a directional representation or to indicate a required physical arrangement of Y or Z with respect to each other, other than a covalent bond. Thus, the attachment of Z to Y is not restricted to the linear representation presented as Y—Z. Rather, Z can be conjugated to, or attached at, the N-terminal end of Y, the C-terminal end of Y, on a side chain of an amino acid that is part of the amino acid sequence of Y, or at any other substitutable position of Y.

In some embodiments, a sequence set forth as one of SEQ ID NOs:1-8, or 23 may be a protected peptide. As used herein, the term "protected peptide" means a peptide that has a structural or chemical feature that protects the peptide from degradation or unwanted reactions in vitro or in vivo under physiological conditions. Thus, the degradation or unwanted reactions of the peptide are inhibited relative to the degradation or unwanted reactions of an unprotected or less protected form of the peptide having the same amino acid sequence.

Examples of features that are considered protective features include, but are not limited to, additions of a chemical protecting group at the N or C terminal of the peptide, and/or the inclusion of stabilized peptide bonds. As used herein, a stabilized peptide bond is a peptide bond that is less amenable to hydrolysis (e.g., enzymatic digestion, etc) than a non-stabilized form of the peptide. Thus, a neuroprotective and/or neurorestorative peptide of the invention can be can be a stabilized peptide that is protected at one or both ends and/or may be protected at the bonds between one or more amino acid residues of the peptide, and/or may have protected amino acid side groups.

As used herein, stabilized means that the bonds linking the amino acids of the peptide are less readily hydrolyzed than peptide bonds formed between L-amino acids. To provide such peptides, one may select isolated peptides from a library of stabilized peptides, such as peptides containing one or more D-amino acids or peptides containing one or more stabilized peptide bonds linking amino acids. Alternatively, one can select peptides that are optimal for a preferred function (e.g., neuroprotective and/or neurorestorative effects) in assay systems described in the Examples and then modify such peptides as necessary to reduce the potential for hydrolysis by proteases. For example, to determine the susceptibility to proteolytic cleavage, peptides may be labeled and incubated with cell extracts or purified proteases and then isolated to determine which peptide bonds are susceptible to proteolysis, e.g., by sequencing peptides and proteolytic fragments. Alternatively, potentially susceptible peptide bonds can be identified by comparing the amino acid sequence of a neuroprotective and/or neurorestorative peptide with the known cleavage site specificity of a panel of proteases. Based on the results of such assays, individual peptide bonds that are susceptible to proteolysis can be replaced with stabilized peptide bonds by in vitro synthesis of the peptide. Preferably the stabilized peptide bonds or amino acids do not alter the neuroprotective and/or neurorestorative activity of the peptides.

Many stabilized peptide bonds (e.g., peptide bonds with reduced level of hydrolyzablity) are known in the art, along with procedures for synthesis of peptides containing such bonds. Stabilized bonds include -psi[CH$_2$NH]— reduced amide peptide bonds, -psi[COCH$_2$]—ketomethylene peptide bonds, -psi[CH(CN)NH]— (cyanomethylene)amino peptide bonds, -psi[CH$_2$CH(OH)]—hydroxyethylene peptide bonds, -psi[CH$_2$O]— peptide bonds, and -psi[CH$_2$S]— thiomethylene peptide bonds.

Neuroprotective and/or neurorestorative peptides of the invention may be administered or delivered independently (as described above) or in some circumstances, it may be preferable to conjugate an isolated peptide having the amino acid sequence set forth as one of SEQ ID NOs:1-8, or 23, protected or not, to a targeting compound, which is a compound that facilitates transport of a peptide of the invention into a cell, and/or facilitates transport of a peptide of the invention across the blood-brain barrier (BBB). In some embodiments, it may be preferable to administer a neuroprotective and/or neurorestorative peptide of the invention in association with (e.g., not conjugated to) a targeting compound. Thus, in some embodiments, a neuroprotective and/or neurorestorative peptide may be administered in association with a targeting compound, but the targeting compound may not be covalently linked to the neuroprotective and/or neurorestorative peptide.

As used herein, the term "facilitate" means "to assist" or "to enable". As used herein, a compound that facilitates transport across the BBB is one that when conjugated to the peptide, enhances the amount of peptide delivered to the brain as compared with non-conjugated peptide. The compound can induce transport across the BBB by any mechanism, including receptor-mediated transport and diffusion. One example of such a mechanism, although not intended to be limiting, is the addition of a lipophilic moiety to a neuroprotective and/or neurorestorative peptide that affects the overall charge characteristics of the molecule facilitating delivery across the blood-brain barrier.

Compounds that are considered to be targeting compounds and may be useful in the methods, kits, and compositions of the invention may include transferrin receptor binding antibodies (U.S. Pat. No. 5,527,527); certain lipoidal forms of dihydropyridine (see, e.g., U.S. Pat. No. 5,525,727); targeting compounds such as cationized albumin or Met-enkephalin (and others disclosed in U.S. Pat. Nos. 5,442,043; 4,902,505; and 4,801,575); cationized antibodies (U.S. Pat. No. 5,004, 697); an acetyl group; an acetyl derivative; a t-butyl acetyl derivative; fatty amines; fatty alcohols; fatty acids such as docosahexaenoic acid (DHA; U.S. Pat. No. 4,933,324) and C8 to C24 fatty acids with 0 to 6 double bonds, glyceryl lipids, cholesterol, polyarginine (e.g., RR, RRR, RRRR) and polylysine (e.g., KK, KKK, KKKK). Unbranched, naturally occurring fatty acids embraced by the invention include C8:0 (caprylic acid), C10:0 (capric acid), C12:0 (lauric acid), C14:0 (myristic acid), C16:0 (palmitic acid), C16:1 (palmitoleic acid), C16:2, C18:0 (stearic acid), C18:1 (oleic acid), C18: 1-7 (vaccenic), C18:2-6 (linoleic acid), C18:3-3 (alpha.-linolenic acid), C18:3-5 (eleostearic), C18:3-6 (&-linolenic acid), C18:4-3, C20:1 (gondoic acid), C20:2-6, C20:3-6 (dihomo-y-linolenic acid), C20:4-3, C20:4-6 (arachidonic acid), C20:5-3 (eicosapentaenoic acid), C22:1 (docosenoic acid), C22:4-6 (docosatetraenoic acid), C22:5-6 (docosapentaenoic acid), C22:5-3 (docosapentaenoic), C22:6-3 (docosahexaenoic acid) and C24: 1-9 (nervonic). Preferred unbranched, naturally occurring fatty acids are those with between 14 and 22 carbon atoms.

Highly preferred compounds that facilitate transport across the BBB include lipoic acid (thiotic acid), docosahexaenoic acid, RRR (arginine string), and KKK (lysine string). The structure of lipoic acid is:

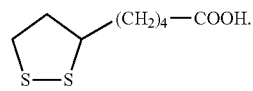

Lipoic acid is indicated as [Lip]- when conjugated to a neuroprotective and/or neurorestorative peptide of the invention. Lipoic acid may be a racemic mixture of d-lipoic acid and l-lipoic acid isomers. In addition, each isomer may be in non-racemic form (e.g., not in mixed with or association with the other lipoic isomer). In some embodiments of the invention, lipoic acid useful to facilitate transport of neuroprotective and/or neurorestorative peptides of the invention across the BBB may be the racemic form. In some embodiments of the invention, an l-lipoic acid may be used to transport a neuroprotective and/or neurorestorative peptide of the invention. In certain embodiments, a d-lipoic acid may be used to transport a peptide of the invention. Thus, in some embodiments, a neuroprotective and/or neurorestorative peptide of the invention may be conjugated to and/or administered with an l-lipoic acid compound and in certain embodiments a neuroprotective and/or neurorestorative peptide of the invention may be conjugated to and/or administered with a d-lipoic acid compound. Thus a composition of the invention comprising a neuroprotective and/or neurorestorative peptide conjugated with lipoic acid may include a mixture of neuroprotective and/or neurorestorative peptides conjugated to d-lipoic acid and l-lipoic acid or may include neuroprotective and/or neurorestorative peptides conjugated to l-lipoic acid or neuroprotective and/or neurorestorative peptides conjugated to d-lipoic acid. It will be understood that a composition of the invention may include one or more different neuroprotective and/or neurorestorative peptides of the invention some of which may be conjugated to targeting compounds. Lipoic acid also has anti-inflammatory properties, which may be useful in methods for augmenting the neuroprotection and/or neurorestorative effects of the peptides of the invention.

Other BBB targeting compounds (e.g. targeting molecules) and methods for conjugating such targeting compounds to peptides will be known to those of ordinary skill in the art. One or more BBB transport molecules can be conjugated to one or more ends of the peptide or to a side chain on an amino acid of the peptide, or onto any other substitutable position on the peptide. As used herein, a substitutable position means a position on a peptide to which a targeting compound can be attached without eliminating the effectiveness of the peptide as a neuroprotective and/or neurorestorative peptide or its usefulness in the methods and/or kits of the invention. Two examples, though not intending to be limiting, of neuroprotective and/or neurorestorative peptides of the invention conjugated to a targeting compound are [Lip]-EVDDDQ (SEQ ID NO:22), and [Lip]-VFTPPS (SEQ ID NO:20), both of which promote neuroprotection from anoxia as described in the Examples section. In some embodiments of the invention, d-lipoic acid may be conjugated to the N-terminal amino acid of a neuroprotective and/or neurorestorative peptide of the invention and in certain embodiments, l-lipoic acid may be conjugated to the N-terminal amino acid of a neuroprotective and/or neurorestorative peptide of the invention. In some embodiments of the invention, an l-lipoic acid or a d-lipoic acid or an racemic mixture of l-lipoic and d-lipoic acid may be administered to a subject in association with (e.g., in combination with, but not conjugated to) a neuroprotective and/or neurorestorative peptide of the invention.

A neuroprotective and/or neurorestorative peptide of the invention (e.g., a peptide with an amino acid sequence set forth as one of SEQ ID NOs:1-8, or 23, protected or not, can be conjugated to targeting compounds by well-known methods, including direct conjugation, conjugation using bifunctional linkers, formation of a fusion polypeptide, and formation of biotin/streptavidin or biotin/avidin complexes by attaching either biotin or streptavidin/avidin to the peptide and the complementary molecule to the targeting compound (e.g., a compound that is cell-entry facilitating and/or BBB-transport facilitating compound). Depending upon the nature of the reactive groups in a peptide and a targeting compound, a conjugate can be formed by simultaneously or sequentially allowing the functional groups of the above-described components to react with one another. For example, a targeting compound can prepared with a sulfhydryl group at, e.g., the carboxyl terminus, which then is coupled to a derivatizing agent to form a targeting molecule. Next, the targeting molecule is attached via its sulfhydryl group, to the peptide. Many other possible linkages are known to those of ordinary skill in the art.

Conjugates of a peptide and a targeting compound may be formed by allowing the functional groups of the compound and the peptide to form a covalent linkage using coupling chemistries known to those of ordinary skill in the art. Numerous art-recognized methods for forming a covalent linkage can be used. See, e.g., March, J., Advanced Organic Chemistry, 4th Ed., New York, N.Y., Wiley and Sons, 1985), pp. 326-1120.

For peptides that exhibit reduced activity in a conjugated form, the covalent bond between the peptides and targeting compound may be selected to be sufficiently labile (e.g., to enzymatic cleavage by an enzyme present in the brain) so that it is cleaved following transport (e.g., following transport of the peptides across the BBB, thereby releasing the free peptides to the brain). Art-recognized biologically labile covalent linkages, e.g., imino bonds, and "active" esters can be used to form prodrugs where the covalently coupled peptides is found to exhibit reduced activity in comparison to the activity of the peptides alone. Exemplary labile linkages are described in U.S. Pat. No. 5,108,921, issued to Low et al., the entire contents of which is incorporated by reference herein.

Other methods for covalently coupling the peptide to the targeting and/or protecting agent include, for example, methods involving glutaraldehyde (Riechlin, Meth. Enzymology 70:159-165, 1980); N-ethyl-N'-(3-dimethylaminopropyl)-carbodiimide (Goodfriend et al., Science 144:1344-1346, 1964); and a mixture of N-ethyl-N'-(3-dimethylaminopropyl)-carbodiimide and a succinylated carrier (Klapper and Klotz, Meth. Enzymol. 25:531-536, 1972). In general, the conjugated peptides of the invention can be prepared by using well-known methods for forming amide, ester or imino bonds between acid, aldehyde, hydroxy, amino, or hydrazo groups on the respective conjugated peptide components. As would be apparent to one of ordinary skill in the art, reactive functional groups that are present in the amino acid side chains of the peptide (and possibly in the transport compound) preferably are protected, to minimize unwanted side reactions prior to coupling the peptide to the targeting and/or protecting agent. Thus, in some embodiments, a protecting group (e.g., protecting molecule) can be bound to a functional group and may be selectively removed therefrom to expose the functional group in a reactive form. In some embodiments, protecting groups are reversibly attached to the functional groups and can be removed therefrom using, for example, chemical or other cleavage methods. Thus, for example, peptides of the invention can be synthesized using commercially available side-chain-blocked amino acids (e.g., FMOC-derivatized amino acids from Advanced Chemtech Inc., Louisville, Ky.). Alternatively, peptide side chains can be reacted with protecting groups after peptide synthesis, but prior to the covalent coupling reaction. In this manner, conjugated peptides of the invention can be prepared in which the amino acid side chains do not participate to any significant extent in the coupling reaction of the peptide to the BBB transport-mediating compound or cell-type-specific targeting agent.

Alternatively, it may be preferable to administer peptides of the invention in combination with a compound that increases transport across the blood-brain bather (BBB). Such compounds, which need not be conjugated to the neuroprotective and/or neurorestorative peptide, increase the transport of the peptide across the BBB into the brain. A compound that increases transport across the BBB is one, for example, that increases the permeability of the BBB, preferably transiently. Coadministration of a peptide with such a compound permits the peptide to cross a permeabilized BBB. Examples of such compounds include bradykinin and agonist derivatives (U.S. Pat. No. 5,112,596); and receptor-mediated permeabilizers such as A-7 (U.S. Pat. Nos. 5,268,164 and 5,506,206).

In some embodiments of the invention, a neuroprotective and/or neurorestorative peptide may be linked to a detectable moiety, such as biotin or a fluorophore, chromophore, enzymatic, and/or radioactive label, and the like. A neuroprotective and/or neurorestorative peptide of the invention linked to a detectible moiety may be useful to monitor cell locations, determine the location of neuronal cell death, determine regions affected in neuronal cell death-associated disease and/or conditions, etc. In some embodiments, a detectably labeled neuroprotective and/or neurorestorative peptide of the invention may be administered to a subject and its location monitored through detection of the label using art-known methods. Detection of labeled neuroprotective and/or neurorestorative peptides of the invention may include in vitro detection in tissue or cell samples, in vivo detection using real-time imaging methods, etc.

A neuroprotective and/or neurorestorative peptide of the invention can be purified from a biological extract, prepared in vitro by recombinant or synthetic means, and/or modified by attachment of a moiety (e.g., a fluorescent, radioactive, or enzymatic label, or an unrelated sequence of amino acids to make a fusion protein) that does not correspond to a portion of the peptide in its native state. Neuroprotective and/or neurorestorative peptides of the invention may also include chimeric proteins comprising a fusion of an isolated peptide with another peptide, e.g., a peptide capable of targeting the isolated peptide to a cell type or tissue type, enhancing stability of the isolated peptide under assay conditions, or providing a detectable moiety, such as green fluorescent protein. A moiety fused to an isolated peptide or a fragment thereof also may provide means of readily detecting the fusion protein, e.g., by immunological recognition or by fluorescent labeling. Purified isolated peptides include peptides isolated by methods including, but not limited to, immunochromotography, HPLC, size-exclusion chromatography, ion-exchange chromatography and immune-affinity chromatography.

Amino acid sequences of neuroprotective and/or neurorestorative peptides of the invention may be of natural or non-natural origin, that is, they may comprise a natural peptide molecule that is a piece of a naturally occurring molecule, may comprise a sequence modified from a naturally occurring molecule, or may be partially or entirely synthetic as long as the peptide has the ability to protect neurons from cell death in a neuronal cell death-associated disease and/or condition. For example, a neuroprotective and/or neurorestorative peptide of the invention may be part of a fusion protein that includes the neuroprotective and/or neurorestorative peptide and unrelated amino acid sequences, synthetic peptides of amino acid sequences provided as SEQ ID NOs:1-8, or 23 (protected or unprotected), labeled peptides, peptides coupled to nonpeptide molecules (for example in certain drug delivery systems).

The term "isolated" as used in connection with nucleic acids that encode peptides embraces all of the foregoing, e.g., isolated nucleic acids are disassociated from adjacent nucleotides with which they are associated in nature, and can be produced recombinantly, synthetically, by purification from biological extracts, and the like. Isolated nucleic acids can contain a portion that encodes one of the foregoing peptides and another portion that codes for another peptide or protein. Isolated nucleic acids also can be labeled. Preferably the nucleic acids include codons that are preferred for mammalian usage. In certain embodiments, the isolated nucleic acid is a vector, such as an expression vector, which includes a nucleic acid that encodes one of the foregoing peptides (e.g., SEQ ID NO:1-8, or 23, protected or unprotected).

Neuroprotective and/or neurorestorative peptides of the invention, such as SEQ ID NOs:1-8, or 23, protected or not, may be synthesized and isolated readily. Those skilled in the art are well versed in methods for preparing and isolating such peptides, such as synthetic chemistry or recombinant biological methods.

Neuroprotective and/or neurorestorative peptides useful in the invention can be linear. In some embodiments, a peptide of the invention may be circular or cyclized by natural or synthetic means and the circular or cyclic peptide may be useful as a neuroprotective and/or neurorestorative peptide. Bifunctional reagents can be used to provide a linkage between two or more amino acids of a peptide. Other methods for cyclization of peptides, such as those described by Anwer et al. (Int. J. Pep. Protein Res. 36:392-399, 1990) and Rivera-Baeza et al. (Neuropeptides 30:327-333, 1996) are also known to those of skill in the art.

It will be understood that in some embodiments of the invention, functional fragments of neuroprotective and/or neurorestorative peptides of the invention are also contemplated for use in the methods and compositions of the invention. Thus, a peptide that is has one or more amino acids deleted from the sequence set forth as SEQ ID NO:1, (e.g., a fragment of SEQ ID NO:1), can be synthesized and tested for neuroprotective and/or neurorestorative function using the methods provided herein. Examples of fragments of SEQ ID NOs:1-8, that may be used in the methods, compositions, and/or kits of the invention are provided as SEQ ID NO: 9-19, 23, and 25-74 in Table 1. Neuroprotective and/or neurorestorative peptide fragments may include, but are not limited to: DDDQ (SEQ ID NO:9), EVDD (SEQ ID NO:10), EV (SEQ ID NO:11), VDDDQ (SEQ ID NO:12) EVDDD (SEQ ID NO:13), DDQ (SEQ ID NO:14), EVD (SEQ ID NO:15), VDDD (SEQ ID NO:16), VDD (SEQ ID NO:17), VD (SEQ ID NO:18), and DD (SEQ ID NO:19).

Nonpeptide analogs of peptides, e.g., those that provide a stabilized structure or lessened biodegradation, are also contemplated. Peptide mimetic analogs can be prepared based on a selected peptide by replacement of one or more residues by nonpeptide moieties. Preferably, the nonpeptide moieties permit the peptide to retain its natural conformation, or stabilize a preferred, e.g., bioactive, conformation. One example of methods for preparation of nonpeptide mimetic analogs from peptides is described in Nachman et al., Regul. Pept. 57:359-370 (1995).

The invention involves, in part, the administration of one or more neuroprotective and/or neurorestorative peptides that reduce neuronal cell death in culture, and reduce the amount of neuronal cell death in tissues and/or subjects. Methods and products of the invention are directed, in part, to reducing the loss of neuronal cells due to death and the loss of neuronal connectivity. Neuroprotective and/or neurorestorative peptides of the invention may restore a population of neuronal cells and/or may protect an existing population from death.

The invention involves, in part, the administration of an effective amount of a neuroprotective and/or neurorestorative peptide of the invention. The neuroprotective and/or neurorestorative peptides of the invention are administered in effective amounts. Typically effective amounts of a neuroprotective and/or neurorestorative peptide will be determined in clinical trials, establishing an effective dose for a test population versus a control population in a blind study. In some embodiments, an effective amount will be that amount that diminishes or eliminates neuronal cell death from a neuronal cell death-associated disease or condition in a cell, tissue, and/or subject. Thus, an effective amount may be the amount that when administered reduces the amount of neuronal cell death from the amount that would occur in the subject or tissue without the administration of the neuroprotective and/or neurorestorative peptide of the invention.

The invention also involves, in part, the administration of a neuroprotective and/or neurorestorative peptide that reduces cell death in cells, tissues, and/or a subject as compared to the amount of neuronal cell death in a control tissue or subject. The invention, in part also relates to the administration of neuroprotective and/or neurorestorative peptides for the treatment of neuronal cell death-associated diseases or conditions. As used herein the term "reduce" or "inhibit" neuronal cell death means to lower or decrease the amount of neuronal cell death. As used herein, to treat a cell, tissue, or subject with a neuronal cell death-associated condition may include the lowering or decreasing of the amount of neuronal cell death to a level or amount that is statistically significant versus a control amount of neuronal cell death. As described elsewhere herein, in some embodiments, a "control" amount may be a reference amount from a subject who has a neuronal cell death-associated disease and a reduction in the amount in a tissue and/or subject may be a decrease in the amount of neuronal cell death to a level or amount that is statistically significantly lower than that control amount. In some cases, the decrease in the amount of neuronal cell death means the amount of neuronal cell death is reduced from an initial amount to a amount statistically significantly lower than the initial amount. In some cases this reduced amount may be, but need not be, zero. In some embodiments, a control amount of cell death may be the amount of cell death in a tissue or subject not subjected to injury or degeneration by toxins or additives. For example, one tissue or subject may be treated in such a way (e.g., chemically [i.e., with toxins or additives], genetically, or mechanically) as to induce neuronal injury or degeneration and contacted with a peptide of the invention to assess the neuroprotective and/or neurorestorative efficacy of the peptide. A control amount of cell death in this example may be the amount present in a substantially similar tissue or subject that is not treated to induce injury or degeneration.

It will be understood by one of ordinary skill in the art that a control amount of neuronal cell death can be a predetermined value, which can take a variety of forms. It can be a single value, such as a median or mean. It can be established based upon comparative groups, such as in disease-free groups that have normal amounts of neuronal cell death. Other comparative groups may be groups of subjects with specific neurological conditions or disease, e.g., PD, AD, brain injury, anoxia, Tardive dyskinesia, cardiovascular disease, macular degeneration, altitude sickness, stroke etc. It will be understood that disease-free cells and/or tissues may be used as comparative groups for cells or tissues that have a neuronal cell death-associated disease or condition.

In some embodiments, a neuroprotective and/or neurorestorative peptide that reduces neuronal cell death is a neuroprotective and/or neurorestorative peptide that reduces or inhibits a neuronal cell death-associated disease or condition. In some embodiments, the amount of neuronal cell death in a tissue and/or subject may be one that is below the amount seen in subjects with symptoms of a neurological disease or a condition, e.g., may be a amount that is clinically asymptomatic. The invention relates in part to the administration of an amount of a neuroprotective and/or neurorestorative peptide of the invention in an amount effective to treat, inhibit, or prevent neuronal cell death of cells and/or in tissues and/or subjects with PD, AD, brain injury, altitude sickness, Tardive dyskinesia, stroke, aging, etc.

Neuroprotective and/or neurorestorative peptides of the invention also include, but are not limited to any pharmaceutically acceptable salts, esters, or salts of an ester of the peptides. Examples of salts that may be used, which are not intended to be limiting include: chloride, acetate, hydrochloride, methansulfonate or other salt of the neuroprotective and/or neurorestorative peptide.

Neuroprotective and/or neurorestorative peptides may also be administered as prodrugs that upon administration to a subject in need of such administration, deliver (directly or indirectly) a pharmaceutically active inhibitor of neuronal cell death as described herein. A pro-drug is a derivative of a compound that contains an additional moiety that is susceptible to removal in vivo yielding the parent molecule as a pharmacologically active agent. An example of a pro-drug is an ester that is cleaved in vivo to yield a compound of interest. Pro-drugs of a variety of compounds, and materials and methods for derivatizing the parent compounds to create the pro-drugs, are known to those of ordinary skill in the art and may be adapted to the present invention.

The invention also involves the use of neuroprotective and/or neurorestorative peptides of the invention in research methods. Examples of such uses include, but are not limited to, the development and testing of cell culture and/or animal models for neuronal cell death-associated diseases and/or conditions and testing for the efficacy of combination treatments and/or therapies for neuronal cell death-associated diseases and/or conditions.

Methods for determining the functional activity of neuroprotective and/or neurorestorative peptides as described herein. The function or status of a neuroprotective and/or neurorestorative peptide as acting to reduce neuronal cell death can be determined according to assays known in the art or described herein. Candidate neuroprotective and/or neurorestorative peptides can be assessed using the methods set forth herein. For example, cells can be contacted with a candidate neuroprotective and/or neurorestorative peptide under conditions that produce neuronal cell death (e.g., in culture or in an animal model of a neuronal cell death-associated disease or injury) and standard procedures can be used to determine whether neuronal cell death amounts are reduced by the neuroprotective and/or neurorestorative peptide. Such methods may also be utilized to determine the functional status of protected forms of a neuroprotective and/or neurorestorative peptide as an inhibitor of neuronal cell death. Although not intended to be limiting, an example of a method with which the ability of a neuroprotective and/or neurorestorative peptide to reduce or inhibit neuronal cell death (and/or loss of neuronal function) can be tested, is an in vitro assay system provided herein in the Examples section.

Using such assays the amount of neuronal cell death (which may be indicated by determining the amount of neuronal function in a tissue or subject) can be measured in the system both before and after contacting the system with a candidate neuroprotective and/or neurorestorative peptide as an indication of the effect of the compound on the amount of neuronal cell death. Secondary screens may further be used to verify the compounds identified as compounds that reduce the amount of neuronal cell death and for use as therapeutics for preventing and/or treating a disease or condition associated with neuronal cell death, e.g., PD, brain injury, stroke, aging, etc.

In addition, protected forms of peptides that are neuroprotective and/or neurorestorative peptides can similarly be tested for their ability to reduce or inhibit neuronal cell death using an in vivo or in vitro assay (see examples). An example of an assay method, although not intended to be limiting, is contacting a tissue or cell sample, under conditions that result in neuronal cell death (e.g., with a neuronal cell death-associated disease, condition, or insult event) with a neuroprotective and/or neurorestorative peptide and determining the peptide's inhibition of neuronal cell death as described herein, and also contacting a similar cell or tissue sample with a protected form of the peptide; determining its amount of inhibition of neuronal cell death, and then comparing the two amounts as a measure of the efficacy of the protected form of the peptide to reduce the amount of neuronal cell death. Neuroprotective and/or neurorestorative peptides of the invention may be utilized in conjunction with cell models of neuronal cell death-associated diseases and/or conditions.

In addition to the in vitro assays described above, in vivo assays may be used to determine the functional activity of neuroprotective and/or neurorestorative peptide as described herein. In such assays, animal models of a neuronal cell death-associated disease, condition, insult, or injury can be treated with a neuroprotective and/or neurorestorative peptide. For example, a neuroprotective and/or neurorestorative peptide set forth herein as SEQ ID NO:2 can be administered to an animal model of a neuronal cell death-associated disease or condition and its functional activity determined in that mode. The amount of cell death or neurological function in the animal can then be assayed using methods described herein or with other art-known methods, useful methods may include labeling or imaging methods, behavioral testing etc. In addition, the amount of neuronal cell death and the effect of a neuroprotective and/or neurorestorative peptide on the amount of neuronal cell death may be assayed more directly by histopathologic examination of brains and tissues. Additionally, animals with and without treatment with a neuroprotective and/or neurorestorative peptide of the invention can be examined for behavior and/or survival as an indication of the effectiveness and/or efficacy of the compounds. Behavior may be assessed by examination of symptoms of aberrant or abnormal amounts of neuronal cell death as described herein. These measurements can then be compared to corresponding measurements in control animals. For example, test and control animals may be examined following administration of a neuroprotective and/or neurorestorative peptide. In some embodiments, test animals are administered a neuroprotective and/or neurorestorative peptide and control animals are not. Any resulting change in amounts of neuronal cell death can then be determined for each type of animal using known methods in the art and as described herein. Such assays may be used to compare amounts of neuronal cell death in animals administered the neuroprotective and/or neurorestorative peptide to control amounts of to neuronal cell death in animals not administered neuroprotective and/or neurorestorative peptide as an indication that the neuroprotective and/or neurorestorative peptide is effective to reduce the amount of neuronal cell death.

A neuroprotective and/or neurorestorative peptide of the invention may be delivered to the cell using standard methods known to those of ordinary skill in the art. Various techniques may be employed for introducing a neuroprotective and/or neurorestorative peptide of the invention to cells, depending on whether the peptide is introduced in vitro or in vivo in a host.

When administered, neuroprotective and/or neurorestorative peptides (also referred to herein as therapeutic compounds and/or pharmaceutical compounds) of the present invention are administered in pharmaceutically acceptable preparations. Such preparations may routinely contain pharmaceutically acceptable concentrations of salt, buffering agents, preservatives, compatible carriers, and optionally other therapeutic agents.

The term "pharmaceutically acceptable" means a non-toxic material that does not interfere with the effectiveness of the biological activity of the active ingredients. The characteristics of the carrier will depend on the route of administration.

The therapeutics of the invention can be administered by any conventional route, including injection or by gradual infusion over time. The administration may, for example, be oral, rectal, vaginal, intravenous, intraperitoneal, intrathecal, intramuscular, intranasal, intracavity, subcutaneous, intradermal, intracerebral, intracranial, or transdermal. Administration may be by any suitable method that allows delivery, directly or indirectly, to the brain, neuronal tissues, and/or nervous system.

Therapeutic compositions may conveniently be presented in unit dosage form and may be prepared by any of the methods well known in the art of pharmacy. Methods include the step of bringing the compounds into association with a carrier that constitutes one or more accessory ingredients. In general, compositions may be prepared by uniformly and intimately bringing the therapeutic agent into association with a liquid carrier, a finely divided solid carrier, or both, and then, if necessary, shaping the product.

Compositions suitable for parenteral administration conveniently comprise a sterile aqueous preparation of the therapeutic agent, which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for oral, subcutaneous, intravenous, intramuscular, etc. can be found in Remington's Pharmaceutical Sciences, Mack Publishing Company, Easton, Pa.

Compositions suitable for oral administration may be presented as discrete units such as capsules, cachets, tablets, or lozenges, each containing a predetermined amount of the therapeutic agent. Other compositions include suspensions in aqueous liquors or non-aqueous liquids such as a syrup, an elixir, or an emulsion. Compositions for delivery may also include suppositories for use in rectal or vaginal delivery.

In some embodiments of the invention, a neuroprotective and/or neurorestorative peptide of the invention may be delivered in the form of a delivery complex. The delivery complex may deliver the neuroprotective and/or neurorestorative peptide into any cell type, or may be associated with a compound and/or molecule for targeting a specific cell type. Examples of delivery complexes include a neuroprotective and/or neurorestorative peptide of the invention associated with: a sterol (e.g., cholesterol), a lipid (e.g., a cationic lipid, virosome or liposome), or a target cell specific binding agent (e.g., an antibody, including but not limited to monoclonal antibodies, or a ligand recognized by target cell specific receptor). Some complexes may be sufficiently stable in vivo to prevent significant uncoupling prior to internalization by the target cell. However, the complex can be cleavable under appropriate conditions within the cell so that the neuroprotective and/or neurorestorative peptide is released in a functional form.

In addition to the targeting methods described above herein, additional targeting and/or delivery methods for a neuroprotective and/or neurorestorative peptide of the invention can be used in the methods of the invention. An example of a targeting method, although not intended to be limiting, is the use of liposomes to deliver a neuroprotective and/or neurorestorative peptide of the invention into a cell. Liposomes may be targeted to a particular tissue, such neuronal cells by coupling the liposome to a specific ligand such as a monoclonal antibody, sugar, glycolipid, or protein. Such proteins include proteins or fragments thereof specific for a particular cell type, antibodies for proteins that undergo internalization in cycling, proteins that target intracellular localization and enhance intracellular half life, and the like.

For certain uses, it may be desirable to target the compound to particular cells, for example specific neuronal cells, which may include targeting specific tissue cell types. In such instances, a vehicle (e.g., a liposome) used for delivering a neuroprotective and/or neurorestorative peptide of the invention to a cell type (e.g., a neuronal cell) may have a targeting compound attached thereto that is an antibody specific for a surface membrane polypeptide of the cell type or may have attached thereto a ligand for a receptor on the cell type. Such a targeting compound can be bound to or incorporated within the neuroprotective and/or neurorestorative peptide delivery vehicle. Where liposomes are employed to deliver the neuroprotective and/or neurorestorative peptides of the invention, proteins that bind to a surface membrane protein associated with endocytosis may be incorporated into the liposome formulation for targeting and/or to facilitate uptake.

Liposomes are commercially available from Invitrogen, for example, as LIPOFECTIN™ and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications.

The invention provides a composition of the above-described agents for use as a medicament, methods for preparing the medicament and methods for the sustained release of the medicament in vivo. Delivery systems can include time-release, delayed release or sustained release delivery systems. Such systems can avoid repeated administrations of the therapeutic agent of the invention, increasing convenience to the subject and the physician. Many types of release delivery systems are available and known to those of ordinary skill in the art. They include polymer-based systems such as polylactic and polyglycolic acid, poly(lactide-glycolide), copolyoxalates, polyanhydrides, polyesteramides, polyorthoesters, polyhydroxybutyric acid, and polycaprolactone. Microcapsules of the foregoing polymers containing drugs are described in, for example, U.S. Pat. No. 5,075,109. Nonpolymer systems that are lipids including sterols such as cholesterol, cholesterol esters and fatty acids or neutral fats such as mono-, di- and tri-glycerides; phospholipids; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

In some embodiments, the preferred vehicle is a biocompatible microparticle or implant that is suitable for implantation into the mammalian recipient. Exemplary bioerodible implants that are useful in accordance with this method are described in PCT International application no. WO 95/24929, entitled "Polymeric Gene Delivery System" describes a biocompatible, preferably biodegradable polymeric matrix for containing an exogenous gene under the control of an appropriate promoter. The polymeric matrix is used to achieve sustained release of the exogenous gene in the patient. Methods of the invention may include administering a nucleic acid that encodes a neuroprotective and/or neurorestorative peptide of the invention to a subject. In accordance with the instant invention, the compound(s) of the invention is encapsulated or dispersed within the biocompatible, preferably biodegradable polymeric matrix disclosed in WO 95/24929. The polymeric matrix preferably is in the form of a microparticle such as a microsphere (wherein the compound is dispersed throughout a solid polymeric matrix) or a microcapsule (wherein the compound is stored in the core of a polymeric shell). Other forms of the polymeric matrix for containing the compounds of the invention include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used. The polymeric matrix composition can be selected to have both favorable degradation rates and also to be formed of a material which is bioadhesive, to further increase the effectiveness of transfer when the device is administered to a vascular surface. The matrix composition also can be selected not to degrade, but rather, to release by diffusion over an extended period of time.

Both non-biodegradable and biodegradable polymeric matrices can be used to deliver agents and compounds of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

Use of a long-term sustained release implant may be particularly suitable for treatment of subjects with an established neurological diseases or conditions as well as subjects at risk of developing a neuronal cell death-associated disease or condition. "Long-term" release, as used herein, means that the implant is constructed and arranged to deliver therapeutic levels of the active ingredient for at least 7 days, and preferably 30-60 days, and most preferably months or years. The implant may be positioned at or near the site of the neurological damage or the area of the brain or nervous system affected by or involved in the neurological disease or condition (e.g., in or near the substantia nigra for subjects with PD). Long-term sustained release implants are well known to those of ordinary skill in the art and include some of the release systems described above.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils.

Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

The preparations of the invention are administered in effective amounts. An effective amount is that amount of a pharmaceutical preparation that alone, or together with further doses, stimulates the desired response. In the case of preventing or treating a disease or condition associated with neuronal cell death, the desired response is reducing the onset, stage, or progression of the disease. This may involve only slowing the progression of the neuronal cell death temporarily, although more preferably, it involves halting the progression of the disease and its associated damage permanently. An effective amount for preventing and/or treating abnormal amounts of neuronal cell death is that amount that statistically significantly reduces the amount or amount of neuronal cell death of a cell, tissue or subject with a neuronal cell death-associated disease or condition, as compared with the amount of neuronal cell death that would occur in the absence of the neuroprotective and/or neurorestorative peptide.

The pharmaceutical compound dosage may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg, and most preferably from about 0.2 mg/kg to about 20 mg/kg, in one or more dose administrations daily, for one or more days.

The absolute amount will depend upon a variety of factors, including the material selected for administration, whether the administration is in single or multiple doses, and individual subject parameters including age, physical condition, size, weight, and the stage of the disease or condition. These factors are well known to those of ordinary skill in the art and can be addressed with no more than routine experimentation.

Pharmaceutical compounds of the invention may be administered alone, in combination with each other, and/or in combination with other drug therapies, or other treatment regimens that are administered to subjects with neuronal cell death-associated disease or conditions such as PD, brain injury, stroke, aging, and/or AD etc. A treatment regimen may be therapeutic strategies exemplified by, but not limited to: surgery, oxygen administration, dialysis, irradiation, etc. Thus, a neuroprotective and/or neurorestorative peptide of the invention may be administered in conjunction with one or more additional drug therapies or treatment regimens for treating a neuronal cell death-associated disease or condition. As will be understood, the term "in conjunction with" means the overall treatment regimens may overlap temporally, thus the drugs and/or treatments may be, but need not be, administered simultaneously. Additional drug therapies (for treatment and/or prophylaxis) that may be administered with pharmaceutical compounds of the invention include, but are not limited to Levodopa (with or without selegiline, amantadine, COMT inhibitors, etc); dopamine agonists (e.g., ropinirole hydrochloride, pramipexole dihydrochloride, etc.); selegiline; amantadine; anticholinergics (e.g., trihexyphenidyl, benztropine mesylate etc.); vitamin E; antioxidant drugs (e.g., vitamin E, vitamin C, bioflavenoids, etc.); tissue plasminogen activator (TPA); clopidogrel; dipyridamole; heparin; ticlopidine; warfarin; acetazolamide (Diamox®); nifedipine (Procardia®); the inhaled drug salmeterol (Serevent®); Sildenafil (Viagra®); dexamethasone; acetaminophen (paracetamol); aspirin; or ibuprofen; amine-depleting drugs (e.g., reserpine, tetrabenazine, etc); branched-chain amino ac (e.g., Tarvil™); benzodiazepines; adrenergic antagonists; etc. It will be understood that two or more neuroprotective and/or neurorestorative compounds of the invention may be administered together in a single therapeutic composition and/or together as part of a treatment regimen.

The above-described putative drug therapies and treatments are known to those of ordinary skill in the art and are administered by modes known to those of skill in the art. The drug therapies and treatments are administered in amounts that are effective to achieve the physiological goals (to reduce symptoms and damage from neuronal cell death-associated disease (e.g., PD, AD, brain injury, stroke etc.) in a subject, in combination with the pharmaceutical compounds of the invention. Thus, it is contemplated that in some embodiments, the additional drug therapies or therapeutic regimens may be administered in amounts which are not capable of preventing or reducing the physiological consequences of the neuronal cell death-associated disease or condition when the drug therapies or regimens are administered alone, but which are capable of preventing or reducing the physiological consequences of neuronal cell death-associated disease when administered in combination with a neuroprotective and/or neurorestorative peptide of the invention. The neuroprotective and/or neurorestorative peptides of the invention can also be provided (e.g., administered) in conjunction with the palliative and supportive therapies for neuronal cell death-associated diseases and/or conditions (e.g., for PD, AD, brain injury, altitude sickness, stroke, aging, etc).

Diagnostic tests known to those of ordinary skill in the art may be used to assess the amount of neuronal cell death in a subject and to evaluate a therapeutically effective amount of a pharmaceutical compound administered. Examples of diagnostic tests include, but are not limited to: neuroimaging methods (e.g., CT scans, MRI, functional MRI etc.) and behavioral screening and testing, etc.

A first determination of a amount of neuronal cell death in a cell, tissue, and/or subject can be obtained using one of the methods described herein (or other methods known in the art, e.g., biochemical and/or morphological methods), and a second, subsequent determination of the amount neuronal cell death can be done. A comparison of the amount of neuronal cell death in the two determinations can be used to assess the effectiveness of administration of a pharmaceutical compound of the invention as a prophylactic or a treatment for a neuronal cell death-associated disease or condition. Family history or prior to occurrence of a neuronal cell death-associated disease or condition, even if the neuronal cell death-associated neurological disease or condition is absent in a subject at present, may be an indication for prophylactic intervention by administering a pharmaceutical compound described herein to reduce or prevent abnormal amounts of neuronal cell death. In the case of some neuronal cell death-associated diseases and/or conditions, genetic testing may be used to assess the likelihood of a subject having a neuronal cell death-associated disease or condition and can be used to determine a need for prophylactic treatment of a subject.

An example of a method of diagnosis of abnormal amounts of neuronal cell death that can be performed using standard methods such as, but not limited to: imaging methods, electrophysiological methods, histological methods, and behavioral assessment and testing. Additional methods of diagnosis and assessment of neuronal cell death-associated disease and the resulting cell death or damage are known to those of skill in the art.

In addition to the diagnostic tests described above, clinical features of neuronal cell death-associated diseases and/or conditions can be monitored for assessment of amounts of neuronal cell death following the onset of a neuronal cell death-associated disease or condition. These features include, but are not limited to: behavioral abnormalities, e.g., movement disorders, memory difficulties etc. Additional features that can be assessed include symptoms such as memory loss, speech disabilities, seizures, poorly articulated speech, difficulty swallowing, disturbances of gait and coordination, fatigue, progressive dementia, progressive stiffness or weakness, as well as the deterioration of brain function. Such assessment of features can be done with methods known to one of ordinary skill in the art, such as behavioral testing and imaging studies, such as radiologic studies, CT scans, PET scans, functional MRI, MRI, etc.

The invention also provides pharmaceutical kits comprising one or more containers comprising one or more of the neuroprotective and/or neurorestorative peptides of the invention and/or formulations of the invention. Kits of the invention may also include instructions for the use of the one or more neuroprotective and/or neurorestorative peptides or formulations of the invention for the treatment of a neuronal cell death-associated disease or condition. Kits of the invention may also comprise additional drugs for preventing and/or treating a neuronal cell death-associated disease or condition. In some embodiments of kits of the invention, the neuroprotective and/or neurorestorative peptide is a neuroprotective and/or neurorestorative peptide that decreases amounts of neuronal cell death. The neuroprotective and/or neurorestorative peptides of the invention may be formulated for delivery to specific cell and/or tissue types. For example, although not intended to be limiting, a neuroprotective and/or neurorestorative peptide of the invention can be formulated for delivery to neuronal cells or to cells in a specific brain region (e.g., the substantia nigra). The neuroprotective and/or neurorestorative peptide in a kit of the invention may also be a neuroprotective and/or neurorestorative peptide that is formulated for sustained release. In some embodiments, the neuroprotective and/or neurorestorative peptide is lyophilized and in some embodiments the neuroprotective and/or neurorestorative peptide is packaged in an aqueous medium.

The invention will be more fully understood by reference to the following examples. These examples, however, are merely intended to illustrate the embodiments of the invention and are not to be construed to limit the scope of the invention.

EXAMPLES

Example 1

Specific Peptides have Neuroprotective Activity in Primary Rat Cortical Cultures Peptides of the invention have been examined for neuroprotective activity in primary rat cortical cultures. The six amino acid long peptide with the amino acid sequence set forth as SEQ ID NO:1 was synthesized and found to be active in reversing the effects of anoxia. It rescued 90-100% of the neurons that were exposed to a 3 hour oxygen-glucose deprivation (OGD). Additional peptides such as VFTPPS (SEQ ID NO:4) and QDDDVE (SEQ ID NO:3) as well as these sequences conjugated to lipoic acid (thiolic acid, e.g. [Lip]-peptide) and acetylated (e.g. [Ac]-peptide) were also tested and found to reverse effects of anoxia.

For the tests, primary mixed neuron-glia rat cortical cultures were grown to 80-95% confluence, as previously described (Shashoua, V. E. et al., Brain Res. (2004) 1024(1-2):34-43). Their neurons were grown over a layer of glia cells and formed a network of processes. Such cultures, after a 5× wash in oxygen-free (air displaced by argon) Hanks Balanced Salt Solution (HBSS) (Shashoua, V. E. et al., Brain Res. (2004) 1024(1-2):34-43) buffer, which contained no glucose, serum, and growth factors, were transferred for 3 hrs into the Form a Scientific Anaerobic Chamber (Thermo Form a, Marietta, Ohio) (Goldberg, M. P. and Choi, D. W. J Neurosei. (1993) 13(8):3510-3524) in an atmosphere of $N_2$, $CO_2$ and $H_2$ (85%, 5%, and 10%). After exposure to oxygen-glucose deprivation (OGD) the neurons, retract their processes and generate vacuoles in their perikarya. Incubation for an additional 21 hrs under normoxia in standard medium did not regenerate the cells. Large increases (about 250%) in the release of lactic acid dehydrogenase (LDH, a marker of cell injury) into the extra-cellular medium occurred. For the test of glucose-oxygen deprivation on the release of lactic acid dehydrogenase as a function of time by primary rat cortical cultures, the LDH assay of extracellular fluid (1 ml aliquots) for cultures from cells were incubated for 24 hours under normoxia conditions and were compared with cells exposed up to 4 hours of anoxia in HBSS medium followed by normoxia medium for a total period of 24 hours. LDH was measured as absorbance at 490 nm, n=6 per time point (Shashoua, V. E. et al., Brain Res. (2004) 1024(1-2):34-43) (see Table 2). Assays and detection were performed according to manufacturer's instructions using a Promega Cyto Tox 96, a nonradioactive cytotoxicity assay kit (Promega, Madison, Wis.).

TABLE 2

Glucose-oxygen deprivation (anoxia) effects on the release of lactic acid dehydrogenase (LDH) as a function of time by primary rat cortical cultures.

| Incubation Time | LDH Assay: Absorbance at 490 nm | |
|---|---|---|
| Hours | Normoxia | Anoxia |
| 1 | 0.002 ± 0.001 | 0.03 ± 0.04 |
| 3 | 0.03 ± 0.01 | 0.08 ± 0.06 |
| 4 | 0.05 ± 0.01 | 0.143 ± 0.1 |

The experiments were repeated with the addition of SEQ ID NO:1 to the media (at concentrations from 1 ng/ml up to 10 ng/ml), even after the 3 hr OGD treatment, all the effects of anoxia were reversed and cell morphology and LDH release returned to normal. For these experiments there were n=6 per assay, and a 3 hour treatment of anoxia was followed by 21 hours of normoxia reperfusion. SEQ ID NO:1 was added at 1 hour post initiation of anoxia and was also present during the 21 hours of reperfusion. SEQ ID NO:1 at high doses decreased LDH release to lower amounts than those present in normoxia controls. The results for SEQ ID NO:1 as well as the results for SEQ ID NOs:3 and 4, which are shown in Tables 3 and 4 give results of LDH assay that was done on supernatant of extracellular medium. The results indicated that the were neuroprotective.

TABLE 3

Effect of SEQ ID NO: 1 on primary rat cortical cultures under conditions of normoxia, anoxia and anoxia plus SEQ ID NO: 1 providing a comparison of LDH release.

| Treatment | SEQ ID NO: 1 Dose (ng/ml) | LDH (A 490 nm) | LDH Released % of Normoxia |
|---|---|---|---|
| Normoxia (control) | 0 | 0.32 ± .01 | 100 |
| Anoxia (OGD control) | 0 | 0.69 ± .06 | 216 |
| Anoxia + SEQ ID NO: 1 | 1 | 0.33 ± .02 | 100 |
| Anoxia + SEQ ID NO: 1 | 10 | 0.22 ± .03 | 68 |
| Anoxia + SEQ ID NO: 1 | 100 | 0.161 ± .04 | 50 |

If the treatment was increased to 100 ng/ml, it was found that LDH release decreased to 50% of the amount released by cells grown under normoxia conditions, suggesting that SEQ ID NO:1 has neurorestorative properties (see Table 3).

TABLE 4

Effect of SEQ ID NOs: 3 and 4 on primary rat cortical cultures under conditions of normoxia, anoxia and anoxia plus SEQ ID NO: 3 or 4, with [Lip]- and [Ac]- as indicated (SEQ ID NO: 21 and 20, respectively). Data provides a comparison of LDH release.

| Treatment | Dose ng/ml | LDH (A 490 nm) | LDH Released % of Normoxia |
|---|---|---|---|
| Normoxia (control) | 0 | 0.33 ± 0.015 | 100 ± 4.5 |
| Anoxia (3 hr control) | 0 | 0.69 ± 0.06 | 209 ± 18 |
| [Lip]-VFTPPS (SEQ NO: 20) 220-63 | 10 | 0.56 ± 0.08 | 169 ± 24 |
|  | 100 | 0.37 ± 0.04 | 112 ± 12 |
| [Ac]-QDDDVE (SEQ NO: 21) 220-61 | 1 | 0.33 ± 0.02 | 100 ± 6 |
|  | 10 | 0.22 ± 0.04 | 67 ± 12 |
|  | 100 | 0.16 ± 0.05 | 48 ± 15 |

Example 2

Studies of the Effect of SEQ ID NO:1 on Dopaminergic Cells Treated with the Neurotoxin MPP+

The possibility that protection from neurotoxicity may also occur for dopaminergic cells was tested in an experiment in collaboration with Prof. A. Kanthasamy at Iowa State University. Here the cultures from N27 dopaminergic cells were treated with 10 μg/ml (14 μM) of SEQ ID NO:1 in the presence of 300 μM of the neurotoxic agent 1-methyl-4-phenylpyridinium (MPP+). The peptide protected the cells from death; cell survival increased by 82% after a 24 hour incubation (Table 5, n=8). Also studies with peptides with sequences similar to SEQ ID NO:1 indicate that neuroprotection is dependant on the specificity of the peptide sequence (compounds SEQ ID NO:21, EV, LE, VE, see Table 6).

TABLE 5

Effect of SEQ ID NO: 1 and its analogues on survival of N27 dopaminergic cells in culture in the presence of 300 μM MPP+ neurotoxic agent. (n = 8)

| Treatment | % Rescue after Treatment for | | |
|---|---|---|---|
|  | 0 hours | 24 hours | 48 hours |
| None (control) | 100 ± 2 | 100 ± 2 | 100 ± 2 |
| 300 μM MPP+ | 100 ± 2 | 0 ± 3 | 0 ± 4 |
| 300 μM MPP+ + 14 μM SEQ ID NO: 1 | 100 ± 2 | 82 ± 2 | 56 ± 4 |

Example 3

Synthesis of Peptides

SEQ ID NO:1 (6 amino acids long), and additional peptides and control peptides are synthesized in 10 mg quantities using the Merrifield solid phase process (Gross, E. and Meienhofer, J. *The Peptides: Analysis, Synthesis*, Biology: Vol. 2, Academic Press, NY, 1983) as described in (Shashoua, V. E. et al., *Brain Res.* (2004) 1024(1-2):34-43). Structures are confirmed by amino acid analysis, migration as a single HPLC peak, and molecular weight determinations by mass spectrometry. A fatty-acid bound N-terminal form of SEQ ID NO:1 is also synthesized. Our previous work (Shashoua, V. E. and Hesse, G. W. *Life Sci.* (1996) 58(16):1347-1357) has shown that the covalent coupling of docosahexaenoic acid (DHA) can improve BBB uptake by a factor of 10 and 100 for dopamine and GABA respectively (Shashoua, V. E. et al., *J Med. Chem.* (1984) 27(5):659-664). Studies are carried out utilizing a variety of fatty acids and the best ones are selected for improving peptide uptake into the brain by the fatty acids' ability to reduce and/or prevent loss of dopamine in pars compacta in the in vivo 1-methyl-4-phenyl-1,2,3,6 tetrahydropyridine (MPTP) mouse model for PD. In each case the MPP+ assay system is first used to determine which form of the peptide gives the best neuroprotection. Once the correct fatty acid is selected synthesis of 1 gram quantities of peptide is done by a commercial source (CS Bio, San Carlos, Calif.) for the in vivo studies.

TABLE 6

Negative Control Experiments Using Modified Peptide Sequences 42 μM Peptide + 300 μM MPP+

| Peptide | SEQ ID NO: 1 Modification | % Rescue per Treatment time | | | Peptide Dose |
|---|---|---|---|---|---|
|  |  | 0 hours | 24 hours | 48 hours |  |
| [Ac]-QDDDVE (SEQ ID NO: 21) | Reversal of sequence | 100 ± 2 | 42 ± 4 | 27 ± 3 | 42 μM |
| EV | dipeptide | 100 ± 2 | 30 ± 7 | ND | 39 μM |
| LE | dipeptide | 100 ± | 27 ± 8 | ND | 39 μM |
| VE | 2 aa from C-terminal | 100 ± 2 | 0 ± 2 | ND | 39 μM |

(ND = not determined; aa = amino acid)

Example 4

Measurement of Neurorestorative Potential of SEQ ID NO:1 and its Analogs in Dopaminergic Cells The dopaminergic cell line (Vila, M. and Przedborski, S. *Nat Rev Neurosci*. (2003) (5):365-375) is also used to determine the neurorestorative effects of the peptides. N27 dopaminergic cells grown in the standard normoxia medium (RPMI 1640 with 10% fetal bovine serum, 2 mM L-glutamine, 50 units of penicillin and 50 mg streptomycin/ml) (Kaul, S. et al., *Eur J Neurosci*. (2003) 18(6):1387-1401), are exposed for various times (0.5, 1, 2, and 3 hours) to OGD in the anoxia chamber, followed by reperfusion, as previously described (Shashoua, V. E. et al., *Brain Res*. (2004) 1024(1-2):34-43), in normal medium and atmosphere. Survival is measured at 24 hours after the start of each experiment. SEQ ID NO:1 restorative effects are indicated when the amount of cell death, as measured by LDH release, is less than that found in the anoxia controls that are stopped at the same time. Each experimental time is compared to a control treated for the same length of anoxia time. The same type of experiment is repeated using MPP+ as the neurotoxic factor. In these studies MPP+ is added at various times to the cultures of N27 and compared with cultures that have no SEQ ID NO:1 or MPP+. The survival of the cells is measured by LDH release at 24 hours. This tests whether partially surviving cultures can be restored to the same level of LDH release as cells that were not treated by MPP+. If the level of survival remains the same as would be expected at the time of addition of SEQ ID NO:1, then the compound would be considered to have neuroprotective properties. If however, the amount of survival increases from this level to approach the level of survival that occurs when the drug is added at the beginning of the experiment then the compound is considered to also have neurorestorative function. SEQ ID NO:1 doses of 1-100 ng/ml are studied (n=6/dose) to obtain statistical significance.

Example 5

In Vivo Experiments: Characterization of the Neuroprotective Efficacy of SEQ ID NO:1 and its Analogs in the MPTP Treated Murine Model of PD Methods
Neurochemical Analysis Neurotransmitters are extracted from striata using 50 μl ice-cold 0.2 M perchloric acid containing 0.1% of disodium EDTA and 10% sodium metabisulfite. Extracts are centrifuged and filtered through 0.2 μm microfilter tubes. Supernatants are then subjected to measurement of dopamine and 3-4-dihydroxyphenylacetic acid (DOPAC) using HPLC-EC method as previously described (Chan, P. et al., *J Pharmacol Exp Ther*. (1993) 267(3):1515-1520; Freyaldenhoven, T. E. et al., *Brain Res*. 1996 735(2):232-238; Kanthasamy, A. G. et al., *Toxicol Appl Pharmacol*. (1994) 126(1):156-163; Kanthasamy, A. G. et al., *Eur J Pharmacol*. 1996 297(3):219-224). Analysis of samples is performed by reverse-phase high performance liquid chromatography (HPLC) coupled with electrochemical detector. Composition of the mobile phase includes 100 mM sodium phosphate, 0.1 mM EDTA, 1.0 mM heptanesulfonic acid, 10% v/v acetonitrile, and 0.01% triethylamine (pH 3.0). 3,4-dihydroxybenzylamine (DHBA) was used as an internal control. Quantitative determination of neurochemical levels were performed using the Dynamic HPLC Method Manager software (Rainin, Woburn, Mass.).

Behavioral Analysis (Locomotor Activity)

Locomotor activity is monitored with a Versamax computerized activity monitoring system (Accusan, Columbus, Ohio) consisting of 16 photocell detectors in both vertical and horizontal dimensions. All experiments are conducted in the light phase and each animal is used only once. The animals are placed in the center of the chamber (42×42×30.5 cm) and preconditioned to the activity monitor for 20 minutes. Immediately following the preconditioning phase, they are automatically screened for horizontal activity for the next 30 minutes. The data is acquired in a computer every 5 minutes through the interface module.

Immunohistochemical Staining

Immunohistochemical analysis is performed as previously described (Freyaldenhoven, T. E. et al., *Brain Res*. (1995) 688(1-2):161-170; Chan, P. et al., *J Pharmacol Exp Ther*. (1993) 267(3):1515-1520; Kanthasamy, A. G. et al., *Eur J Pharmacol*. (1996) 297(3):219-224). After the treatment, the animals are sacrificed, brains fixed by transcardial perfusion with 4% paraformaldehyde in PBS and then post-fixed in the same solution for at least 12 hours. Series of adjacent 40μ meter sections are obtained through the rostrocaudal extent of the midbrain dopaminergic regions and then washed three times with 0.1 M PBS, pH 7.4. The sections are permeabilized with 0.2% Triton X-100 and are incubated with TH antibody (1:2000) overnight at 4° C. followed by incubation with Cy3- or Alexa-488 conjugated secondary antibody for 1 hour. The immunofluorescence is observed under a Nikon microscope and cells counted as described in previous publications (Kanthasamy, A. G. et al., *Brain Res*. (1997) 759(1):1-8; Kanthasamy, A. G. et al., *Neurotoxicology*. (1991) 12(4):777-784).

Analysis of MPP+

The MPP+ content in the striatum and ventral mesencephalon is measured as previously described (Freyaldenhoven, T. E. et al., *Brain Res*. (1995) 688(1-2):161-170). The tissues are weighed and placed in an ice-cold solution 250 μl 0.1 M perchloric acid containing 150 ng/ml of 1-butyl-4-phenylpyridinium as an internal standard. The tissues are disrupted and homogenized using a microtip-sonicator for 20 seconds, and then centrifuged at 10,500 g for 20 minutes. The supernatant is analyzed for MPP+ using HPLC coupled with a spectrophotometric detector. The wave length is set at 290 nm. The mobile phase for HPLC consists of 100 mM sodium acetate, 30% v/v acetonitrile and 0.01% triethylamine. Quantitative determination of the MPP+ level is calculated with software through comparisons of sample peak area with peak area of known amounts of the internal standard.

Molecular Mechanism Studies

The Affymetrix Genomic Core Facility at the University of Massachusetts Medical

School is utilized to study effects of MPP+ with and without added SEQ ID NO:1, SEQ ID NO:1 alone and non-drug treated controls in the N27 dopaminergic cultures. Total RNA from such cultures is extracted using the Qiagen RNeasy mini kit and delivered as a pellet under ethanol to the Core Facility for analysis on chip #2 total rat genome. The changes in protein kinase c, BCl2 and other genes are identified and then investigated in culture. The gene chip assay has been shown to be 95-98% reproducible (He, F. et al., *Mol. Cell*. (2003) 12(6):1439-1452).

Results

Two drugs, an acetylated and a lipid form of SEQ ID NO:1 are tested in the MPTP treated C57 black mice as the animal model. Adult C57 black mice are pre-screened for baseline locomotion and grouped into groups of ten animals each. MPTP, at a dose of 30 mg/kg i.p., is administered once daily for 5 consecutive days to treatment groups. The acetylated and lipid forms of SEQ ID NO:1 and its analogs identified to have neuroprotective potential in N27 cells are administered 15 minutes after each MPTP treatment. This post-treatment approach should generate more relevant information than a pre-treatment regimen. Dose ranges for in vivo studies are extrapolated from EC50 values obtained using the cell culture model. A minimum of three doses per drug are administered. The control groups will receive equal volumes of normal saline or vehicle (IV). After 5 days of treatment, locomotor activity is measured by using the Versamax computerized locomotor activity monitor on day 6. Following behavioral measurements, animals are sacrificed. The striatal dopamine and DOPAC levels, and tyrosine hydroxylase immunopositive cells present in striatum are measured and compared between treatment groups. The physiological basis of neuroprotection is distinguished from environmental and/or pharmacokinetic influences of the pharmacological agents. Administration of MPTP produces transient hyperthermia followed by more prolonged hyperthermia (Freyaldenhoven, T. E. et al., *Brain Res.* (1995) 688(1-2):161-170). Blockade of initial hyperthermia accentuates the MPTP induced toxicity (Freyaldenhoven, T. E. et al., *Brain Res.* (1995) 688(1-2):161-170). Therefore, body temperature is monitored at different time intervals (30, 90, 120 minutes) following administration of the experimental drugs. When evaluating the neuroprotective agents in the MPTP model, whether the test compound alters MPP+ accumulation in the target tissue is also considered. Such an alteration can influence the neurotoxicity of MPP+ (Shashoua, V. E. et al., *J Med. Chem.* (1984) 27(5): 659-664; Freyaldenhoven, T. E. et al., *Brain Res.* (1995) 688(1-2):161-170). Therefore, MPP+ levels in the striatum are examined using HPLC-fluorescence measurements.

Example 6

A characteristic constituent of Alzheimer's Disease (AD) is the formation of plaques from the 39-43 amino acid long peptide derived from amyloid protein (Selkoe, D. *TINS* (1993) 16: 403-409). This molecule (b/A4) can be toxic to mammalian nerve cells. Yankner et al., (1990) *Science* 250: 279-282) have demonstrated that b/A4 can be toxic to primary rat hippocampal cells in culture, causing degeneration and an increase of the AD-related tau protein (Kosik *Science* (1992) 256: 780-783). Yankuer et al. (*Science* (1990) 250: 279-282) has developed this property in a culture method as an AD assay procedure. We have adapted this to test the efficacy of SEQ ID NO: 2 as a neuroprotective and/or neurorestorative peptide in the AD culture model. Lambert et al (*J Neurosci Res* 1994 39: 377-385) has demonstrated that b/A4 can evoke degeneration of differentiated SH-SY5Y Human Neuroblastoma cells.

In conjunction with Prof David Adams (WPI. Worcester, Mass.), the following two methods have been used to test the efficacy of SEQ ID NO: 2 in protecting SH-SY5Y human neuroblastoma cells from the toxic effects if b/A4.
Experiment 1
Methods
Differentiated cultures of SH-SY5Y Human neuroblastoma cells were grown to a stage where the cells formed a network of neurites. The cultures consisting of an untreated control, and two experimental groups (1) treated with b/A4 and (2) with b/A4+SEQ ID NO: 2. At day 3, after removal of the supernatant and the debris from dead cells by 3 washes with saline, the cells were then lysed and their LDH content was assayed for cell survival by measuring the LDH present in the remaining cells. The results were compared to LDH present in untreated controls, that were incubated for 3 days with no peptide additives (Table 7). The assay assumes that the LDH content of healthy cells remains constant and can be used as an index of living cells. The experiments using anoxia in our previous work were in agreement with this assumption.
Results

TABLE 7

Treatment of neuroblastoma cells with SEQ ID NO: 2.

| Sample | Peptide Dose | OD 490 nm | % Survival |
|---|---|---|---|
| Control | none | 0.860 | 100% |
| Yankner peptide | 20 µM | 0.568 | 66% |
| SEQ ID NO: 2 + Yankner | 0.4 µM 20 µM | 0.935 | 100% |

These results indicate that the SH-SY5Y neuroblastoma cells are protected by SEQ ID NO: 2 from the toxic effects of the Yankner peptide.
Experiment 2
Methods
This experiment was performed in the method described above for Example 6, Experiment 1, except that the cells were incubated for 4 days instead of 3 to enhance the degenerative effect of the Yankner peptide. At the end of the experiment the cultures were washed in saline containing 0.01% triton X-100 to remove all released LDH and cellular debris before lysis and analysis for LDH content of the surviving cells (Table 8).
Results

TABLE 8

Treatment of neuroblastoma cells with SEQ ID NO: 2.

| Sample | Peptide Dose | OD 490 nm | % Survival |
|---|---|---|---|
| Control | none | 0.448 | 100% |
| Yankner peptide | 20 µM | 0.127 | 28.3% |
| SEQ ID NO: 2 + Yankner | 0.4 µM 20 µM | 0.287 | 64.1% |

These results, presented in Tables 7 and 8, indicated that SEQ ID NO: 2 is potentially useful as a candidate drug for treatment of AD.

Example 7

Introduction

In a tissue culture model for Alzheimer's disease, treatment with the Yankner peptide (amyloid fragment) causes cell death within 3 days. Addition to human neuroblastoma cells of a neuroprotective and/or neurorestorative peptide of the invention (BTX peptide) together with the amyloid fragment, rescued the cells from cell death. By studying the time course of cell death in this culture model for Alzheimer's disease, it was determined that about 60% of the cells die within 24 hrs. When the neuroprotective/neurorestorative peptide of the invention was added to the cells at the 24 hour time point (e.g., 24 hours after the cells were contacted with the Yankner peptide), over 40% of the injured neurons that were destined to die on day 3 were rescued. This suggests that the BTX peptide had neuro-restorative as well as neuro-protective effects.

Experiment 1
Effects of Neuroprotective/Neurorestorative Peptides on SHSY Cell Numbers In Vitro.

Aliquots of $3 \times 10^5$ SHSY cells were plated in each well of a 24-well microtiter plate in 1 ml of medium containing no peptides (Control=Ctrl), 20 μM Yankner peptide (Yankner), or 20 μM Yankner peptide+75 μM of DQ (SEQ ID NO:2) (Yanlmer+BTX). Plates were incubated at 37° C. in a 5% $CO_2$ incubator for 3 days, then each well was washed twice with 1×PBS to remove loosely bound cells. The number of remaining cells per ml was determined by microscopy. Each histobar in FIG. 1 represents the mean of four independent measures. Error bars denote one standard deviation. The following p values were obtained using a two-tailed student's t-test: Ctrl vs Yankner 0.005; Yankner vs Yankner+BTX 0.006; Ctrl vs Yankner+BTX 0.03. BTX was DQ (SEQ ID NO:2) in this experiment.
Experiment 2

Figure 2:
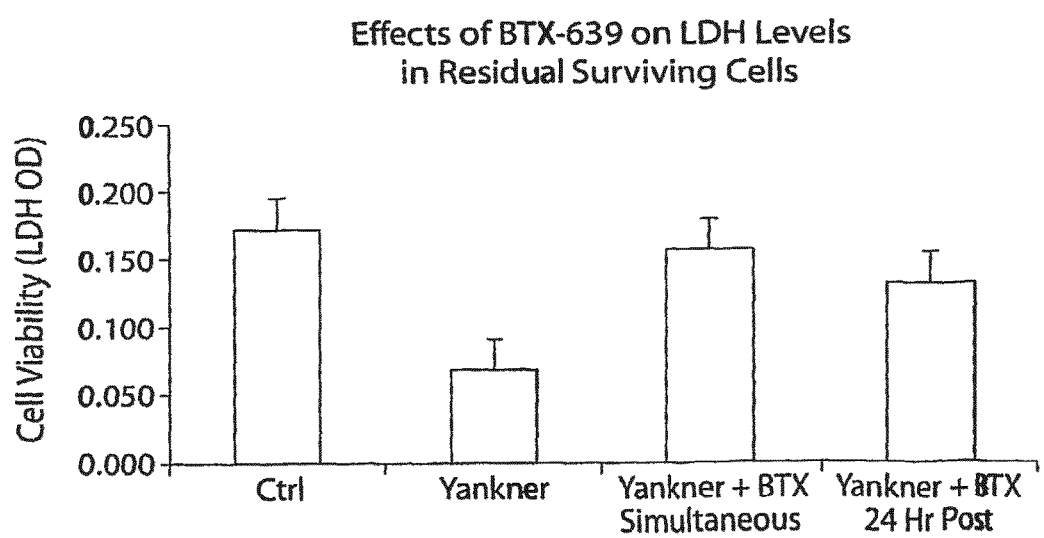
FIG. 2 is a histogram demonstrating the effects of BTX-639 [peptide DQ (SEQ ID NO:2)] on LDH levels in residual surviving cells. Each histobar represents the mean of 11 independent trials. Error bars denote one standard deviation. The following p values were obtained using a two-tailed student's t-test: Ctrl vs Yankner 0.0002; Yankner vs Yankner+BTX Simultaneous 0.00004; Yankner vs Yankner+BTX 24 Hr Post 0.02. BTX=peptide DQ (SEQ ID NO:2) ctrl=control.

Effects of DQ Peptide (SEQ ID NO:2) (BTX-Drug) on LDH Levels in Residual Surviving Cells In Vitro Aliquots of $3 \times 10^5$ SHSY cells were plated in each well of a 24-well microtiter plate in 1 ml of medium containing no peptides (control=Ctrl), 20 μM Yankner peptide (Yanlmer), 20 μM Yanlmer peptide+75 μM DQ peptide (SEQ ID NO:2) added at time of plating (Yankner+BTX Simultaneous), or 20 μM Yankner+75 μM BTX-639 added 24 hr post plating (Yankner+BTX 24 Hr Post). Plates were incubated at 37° C. in a 5% $CO_2$ incubator for 3 days, then each well was washed twice with 1×PBS to remove loosely bound cells. Whole cell lysates were prepared from the remaining attached (viable) cells, and Lactate dehydrogenase (LDH) activity measured as described in methods. The results are illustrated in FIG. 2, in which each histobar represents the mean of 11 independent trials. Error bars denote one standard deviation. The following p values were obtained using a two-tailed student's t-test: Ctrl vs Yankner 0.0002; Yankner vs Yankner+BTX Simultaneous 0.00004; Yankner vs Yankner+BTX 24 Hr Post 0.02. BTX and BTX-639 were DQ (SEQ ID NO:2) in this experiment.
Discussion The results of Experiments 1 and 2 demonstrated that the BTX peptides had neuroprotective and neurorestorative effects. The results also demonstrated that the BTX peptides were not stimulants of cell division, suggesting that the peptide's effect in blocking cell death caused by the Yankner peptide was not due to replacement of the dead cells by new cells.

Example 8

Effect of Peptide AA (SEQ ID NO:23) on Toxicity in Cell Culture Model of Alzheimer's Disease Experiments were performed that demonstrated that the dipeptide AA (SEQ ID NO:23) can prevent the toxicity of the Yankner peptide in neuroblastoma cells with a similar efficacy as the peptide DQ (SEQ ID NO:2). The neuroblastoma cultures (as described in Example 7, Experiment 1) were treated with 20 μM Yankner peptide with and without the simultaneous addition of peptide AA (SEQ ID NO:23). Yankner alone caused a 50% cell death, whereas 104% of the drug-treated cells survived.

Example 9

Effects of DQ (SEQ ID NO:2) on Cellular Levels of Caspase-3

Figure 3:
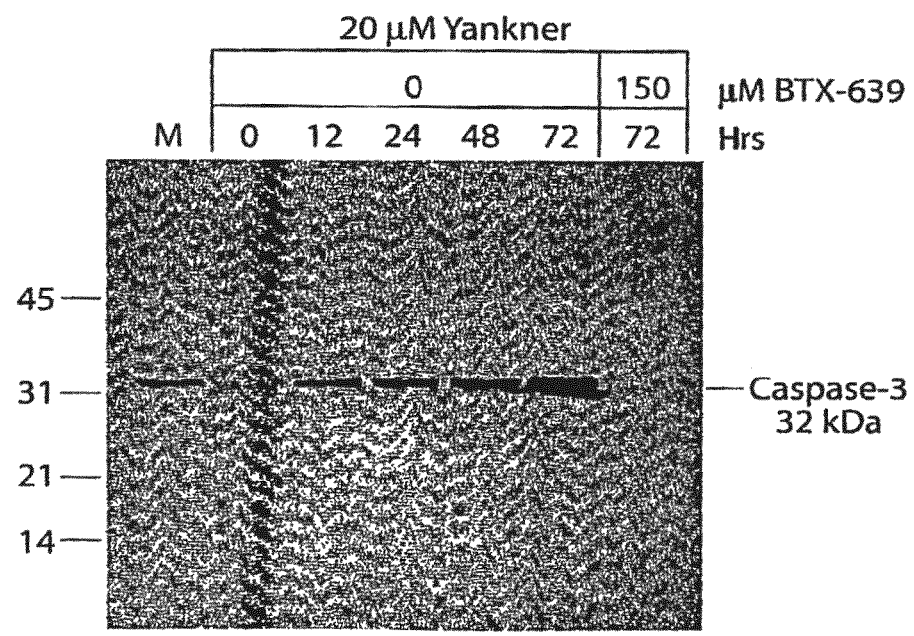
FIG. 3 is a digitized image of a immunoblot demonstrating the effect of BTX-639 [peptide DQ (SEQ ID NO:2)] on cellular level of Caspase-3. M=Marker lane, middle lanes=20 µM Yankner peptide (at various times), and the right lane=20 µM Yankner+BTX-639. The numbers to the left of the figure denote the sizes in kDa of the marker protein (Biorad Broad Scope). The position of Caspase-3 at the expected size of 32 kDa is denoted on the right of the blot.

Aliquots of $2 \times 10^6$ SHSY cells were plated into each of 7 T-25 cell culture flasks with 5 ml of medium containing 2 mM Staurosporine (a known neuronal apoptosis stimulator). Results are shown in FIG. 3 with (Marker lane M), 20 μM Yankner peptide (middle lanes), and 20 μM Yankner+BTX-639 (right lane). Flasks were incubated at 37° C. in a 5% $CO_2$ incubator for 0, 12, 24, 48, or 72 hours (as indicated in FIG. 3), then whole cell lysates were prepared as described in Methods. Caspase-3 immuoblots were performed on 20 μg of total cellular protein per lane. Numbers to the left of the figure denote the sizes in kDa of the marker protein (Biorad Broad Scope). The position of Caspase-3 at the expected size of 32 kDa is denoted on the right of the figure. BTX-639 is the peptide DQ (SEQ ID NO:2). The results showed that DQ (SEQ ID NO:2) reduced the effect of the Yankner peptide on the level of Caspase-3 in the cells indicating that the peptide DQ (SEQ ID NO:2) is a strong Caspase-3 Synthesis Inhibitor and blocks apoptosis.

Example 10

Survival of Noradrenergic Neurons in the MPTP Mouse Model for Parkinson's Disease In vivo tests of [Lip]-EVDDDQ in mice showed that the compound increases the survival of noradrenergic neurons in the striatum by 2.2-fold (10% viable in control, versus 26.9% viable when peptide added). Tests were done in the MPTP mouse model for Parkinson's disease.

These in vivo tests showed that only 12.5% of the neurons can survive after a 4-days following an IP injection 30 mg/Kg of MPTP into the mouse model of PD. When this was accompanied with a dose of [Lip]-EVDDDQ (SEQ ID NO:22) followed by a daily additional dose of [Lip]-EVDDDQ (SEQ ID NO:22), the survival of noradrenergic cells in the Pars Compacta region of the striatum, increased to 26.9% (n=5). This is a significant improvement demonstrated that the lipoic acid derivative of EVDDDQ (SEQ ID NO:1) can get through the Blood-Brain Barrier (BBB).

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

I claim:

1. A method for inhibiting neuronal cell death, the method comprising:
contacting neuronal cells with a neuroprotective peptide in an amount effective to inhibit the death of the neuronal cells, wherein the neuroprotective peptide is Y—$Z_N$, in which Y is a peptide moiety having the amino acid sequence of DQ (SEQ ID NO:2) or AA (SEQ ID NO:23), Z is a targeting compound moiety, and N is 0, 1, 2, or 3, wherein the death of the neuronal cells is associated with Parkinson's disease or Alzheimer's disease.

2. The method of claim 1, wherein the death of the neuronal cells is associated with Alzheimer's disease.

3. The method of claim 1, wherein the contacting step is performed by administering the neuroprotective peptide to a subject in need thereof.

4. The method of claim 3, wherein the subject has or is suspected of having neuronal cell death associated with Alzheimer's disease.

5. The method of claim 1, wherein the targeting compound moiety is selected from the group consisting of docosohexaenoic acid, lipoic acid, a transferrin receptor binding antibody, cationized albumin, Met-enkephalin, a dihydropyridine in lipoidal form, a cationized antibody, an acetyl group, an acetyl derivative, and a t-butyl acetyl derivative.

6. The method of claim 1, wherein the neuroprotective peptide is a protected peptide, which includes one or more D-amino acids, a -psi[$CH_2NH$]-reduced amide peptide bond, a -psi[$COCH_2$]— ketomethylene peptide bond, a -psi[CH(CN)NH]— (cyanomethylene)amino peptide bond, a -psi[$CH_2CH(OH)$]— hydroethylene peptide bond, a psi[$CH_2O$]— peptide bond, or a psi[$CH_2S$]— thiomethylene peptide bond.

7. The method of claim 6, wherein the protected peptide is an N or C terminal protected peptide.

8. The method of claim 1, wherein the neuroprotective peptide is a protected peptide, which is an N-acetylated peptide.

9. The method of claim 1, wherein N is 1 or 2.

10. A method for treating Alzheimer's disease in a subject, the method comprising:
administering to a subject in need thereof an effective amount of a neuroprotective peptide, wherein the neuroprotective peptide is Y—$Z_N$, in which Y is a peptide moiety having the amino acid sequence of DQ (SEQ ID NO:2) or AA (SEQ ID NO:23), Z is a targeting compound moiety, and N is 0, 1, 2, or 3.

11. The method of claim 10, wherein the neuroprotective peptide is in an amount effective to inhibit neuronal cell death associated with Alzheimer's disease in the subject.

12. The method of claim 10, wherein the targeting compound moiety is selected from the group consisting of docosohexaenoic acid, lipoic acid, a transferrin receptor binding antibody, cationized albumin, Met-enkephalin, a dihydropyridine in lipoidal form, a cationized antibody, an acetyl group, an acetyl derivative, and a t-butyl acetyl derivative.

13. The method of claim 10, wherein the neuroprotective peptide is a protected peptide, which includes one or more D-amino acids, a -psi[$CH_2NH$]— reduced amide peptide bond, a -psi[$COCH_2$]— ketomethylene peptide bond, a -psi[CH(CN)NH]— (cyanomethylene)amino peptide bond, a -psi[$CH_2CH(OH)$]— hydroethylene peptide bond, a psi[$CH_2O$]— peptide bond, or a psi[$CH_2S$]— thiomethylene peptide bond.

14. The method of claim 13, wherein the protected peptide is an N or C terminal protected peptide.

15. The method of claim 10, wherein the neuroprotective peptide is a protected peptide, which is an N-acetylated peptide.

16. The method of claim 10, wherein N is 1 or 2.

* * * * *

SEQUENCE LISTING

<160> NUMBER OF SEQ ID NOS: 74

<210> SEQ ID NO 1
<211> LENGTH: 6

```
<212> TYPE: PRT
<213> ORGANISM: Artificial sequence
<220> FEATURE:
<223> OTHER INFORMATION: Synthetic Peptide

<400> SEQUENCE: 1

Glu Val Asp Asp Gln
1               5

<210> SEQ ID NO 2
<211> LENGTH: 2
<212> TYPE: PRT
<213> ORGANISM: Artificial sequence
<220> FEATURE:
<223> OTHER INFORMATION: Synthetic Peptide

<400> SEQUENCE: 2

Asp Gln
1

<210> SEQ ID NO 3
<211> LENGTH: 6
<212> TYPE: PRT
<213> ORGANISM: Artificial sequence
<220> FEATURE:
<223> OTHER INFORMATION: Synthetic Peptide

<400> SEQUENCE: 3

Gln Asp Asp Asp Val Glu
1               5

<210> SEQ ID NO 4
<211> LENGTH: 6
<212> TYPE: PRT
<213> ORGANISM: Artificial sequence
<220> FEATURE:
<223> OTHER INFORMATION: Synthetic Peptide

<400> SEQUENCE: 4

Val Phe Thr Pro Pro Ser
1               5

<210> SEQ ID NO 5
<211> LENGTH: 4
<212> TYPE: PRT
<213> ORGANISM: Artificial sequence
<220> FEATURE:
<223> OTHER INFORMATION: Synthetic Peptide

<400> SEQUENCE: 5

Asp Asp Val Glu
1

<210> SEQ ID NO 6
<211> LENGTH: 4
<212> TYPE: PRT
<213> ORGANISM: Artificial sequence
<220> FEATURE:
<223> OTHER INFORMATION: Synthetic Peptide

<400> SEQUENCE: 6

Arg Phe Gln Leu
1

<210> SEQ ID NO 7
<211> LENGTH: 6
<212> TYPE: PRT
```

```
<213> ORGANISM: Artificial sequence
<220> FEATURE:
<223> OTHER INFORMATION: Synthetic Peptide

<400> SEQUENCE: 7

Gln Leu Asp Asp Val Glu
1               5

<210> SEQ ID NO 8
<211> LENGTH: 6
<212> TYPE: PRT
<213> ORGANISM: Artificial sequence
<220> FEATURE:
<223> OTHER INFORMATION: Synthetic Peptide

<400> SEQUENCE: 8

Arg Phe Gln Leu Thr Glu
1               5

<210> SEQ ID NO 9
<211> LENGTH: 4
<212> TYPE: PRT
<213> ORGANISM: Artificial sequence
<220> FEATURE:
<223> OTHER INFORMATION: Synthetic Peptide

<400> SEQUENCE: 9

Asp Asp Asp Gln
1

<210> SEQ ID NO 10
<211> LENGTH: 4
<212> TYPE: PRT
<213> ORGANISM: Artificial sequence
<220> FEATURE:
<223> OTHER INFORMATION: Synthetic Peptide

<400> SEQUENCE: 10

Glu Val Asp Asp
1

<210> SEQ ID NO 11
<211> LENGTH: 2
<212> TYPE: PRT
<213> ORGANISM: Artificial sequence
<220> FEATURE:
<223> OTHER INFORMATION: Synthetic Peptide

<400> SEQUENCE: 11

Glu Val
1

<210> SEQ ID NO 12
<211> LENGTH: 5
<212> TYPE: PRT
<213> ORGANISM: Artificial sequence
<220> FEATURE:
<223> OTHER INFORMATION: Synthetic Peptide

<400> SEQUENCE: 12

Val Asp Asp Asp Gln
1               5

<210> SEQ ID NO 13
<211> LENGTH: 5
<212> TYPE: PRT
<213> ORGANISM: Artificial sequence
```

```
<220> FEATURE:
<223> OTHER INFORMATION: Synthetic Peptide

<400> SEQUENCE: 13

Glu Val Asp Asp Asp
1               5

<210> SEQ ID NO 14
<211> LENGTH: 3
<212> TYPE: PRT
<213> ORGANISM: Artificial sequence
<220> FEATURE:
<223> OTHER INFORMATION: Synthetic Peptide

<400> SEQUENCE: 14

Asp Asp Gln
1

<210> SEQ ID NO 15
<211> LENGTH: 3
<212> TYPE: PRT
<213> ORGANISM: Artificial sequence
<220> FEATURE:
<223> OTHER INFORMATION: Synthetic Peptide

<400> SEQUENCE: 15

Glu Val Asp
1

<210> SEQ ID NO 16
<211> LENGTH: 4
<212> TYPE: PRT
<213> ORGANISM: Artificial sequence
<220> FEATURE:
<223> OTHER INFORMATION: Synthetic Peptide

<400> SEQUENCE: 16

Val Asp Asp Asp
1

<210> SEQ ID NO 17
<211> LENGTH: 3
<212> TYPE: PRT
<213> ORGANISM: Artificial sequence
<220> FEATURE:
<223> OTHER INFORMATION: Synthetic Peptide

<400> SEQUENCE: 17

Val Asp Asp
1

<210> SEQ ID NO 18
<211> LENGTH: 2
<212> TYPE: PRT
<213> ORGANISM: Artificial sequence
<220> FEATURE:
<223> OTHER INFORMATION: Synthetic Peptide

<400> SEQUENCE: 18

Val Asp
1

<210> SEQ ID NO 19
<211> LENGTH: 2
<212> TYPE: PRT
<213> ORGANISM: Artificial sequence
<220> FEATURE:
```

```
<223> OTHER INFORMATION: Synthetic Peptide

<400> SEQUENCE: 19

Asp Asp
1

<210> SEQ ID NO 20
<211> LENGTH: 6
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: [Lip]-Val

<400> SEQUENCE: 20

Val Phe Thr Pro Pro Ser
1               5

<210> SEQ ID NO 21
<211> LENGTH: 6
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: [Ac]-Gln

<400> SEQUENCE: 21

Gln Asp Asp Asp Val Glu
1               5

<210> SEQ ID NO 22
<211> LENGTH: 6
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: [Lip]-Glu

<400> SEQUENCE: 22

Glu Val Asp Asp Asp Gln
1               5

<210> SEQ ID NO 23
<211> LENGTH: 2
<212> TYPE: PRT
<213> ORGANISM: Artificial sequence
<220> FEATURE:
<223> OTHER INFORMATION: Synthetic Peptide

<400> SEQUENCE: 23

Ala Ala
1

<210> SEQ ID NO 24
<211> LENGTH: 2
<212> TYPE: PRT
<213> ORGANISM: Artificial sequence
<220> FEATURE:
<223> OTHER INFORMATION: Synthetic Peptide
<220> FEATURE:
```

```
<221> NAME/KEY: MISC_FEATURE
<222> LOCATION: (1)..(1)
<223> OTHER INFORMATION: [Lip]-Asp

<400> SEQUENCE: 24

Asp Gln
1

<210> SEQ ID NO 25
<211> LENGTH: 2
<212> TYPE: PRT
<213> ORGANISM: Artificial sequence
<220> FEATURE:
<223> OTHER INFORMATION: Synthetic Peptide

<400> SEQUENCE: 25

Gln Asp
1

<210> SEQ ID NO 26
<211> LENGTH: 3
<212> TYPE: PRT
<213> ORGANISM: Artificial sequence
<220> FEATURE:
<223> OTHER INFORMATION: Synthetic Peptide

<400> SEQUENCE: 26

Gln Asp Asp
1

<210> SEQ ID NO 27
<211> LENGTH: 3
<212> TYPE: PRT
<213> ORGANISM: Artificial sequence
<220> FEATURE:
<223> OTHER INFORMATION: Synthetic Peptide

<400> SEQUENCE: 27

Asp Asp Asp
1

<210> SEQ ID NO 28
<211> LENGTH: 4
<212> TYPE: PRT
<213> ORGANISM: Artificial sequence
<220> FEATURE:
<223> OTHER INFORMATION: Synthetic Peptide

<400> SEQUENCE: 28

Asp Asp Val Glu
1

<210> SEQ ID NO 29
<211> LENGTH: 3
<212> TYPE: PRT
<213> ORGANISM: Artificial sequence
<220> FEATURE:
<223> OTHER INFORMATION: Synthetic Peptide

<400> SEQUENCE: 29

Asp Val Glu
1

<210> SEQ ID NO 30
<211> LENGTH: 4
<212> TYPE: PRT
<213> ORGANISM: Artificial sequence
```

```
<220> FEATURE:
<223> OTHER INFORMATION: Synthetic Peptide

<400> SEQUENCE: 30

Asp Asp Asp Val
1

<210> SEQ ID NO 31
<211> LENGTH: 5
<212> TYPE: PRT
<213> ORGANISM: Artificial sequence
<220> FEATURE:
<223> OTHER INFORMATION: Synthetic Peptide

<400> SEQUENCE: 31

Asp Asp Asp Val Glu
1               5

<210> SEQ ID NO 32
<211> LENGTH: 4
<212> TYPE: PRT
<213> ORGANISM: Artificial sequence
<220> FEATURE:
<223> OTHER INFORMATION: Synthetic Peptide

<400> SEQUENCE: 32

Gln Asp Asp Asp
1

<210> SEQ ID NO 33
<211> LENGTH: 5
<212> TYPE: PRT
<213> ORGANISM: Artificial sequence
<220> FEATURE:
<223> OTHER INFORMATION: Synthetic Peptide

<400> SEQUENCE: 33

Gln Asp Asp Asp Val
1               5

<210> SEQ ID NO 34
<211> LENGTH: 2
<212> TYPE: PRT
<213> ORGANISM: Artificial sequence
<220> FEATURE:
<223> OTHER INFORMATION: Synthetic Peptide

<400> SEQUENCE: 34

Asp Val
1

<210> SEQ ID NO 35
<211> LENGTH: 2
<212> TYPE: PRT
<213> ORGANISM: Artificial sequence
<220> FEATURE:
<223> OTHER INFORMATION: Synthetic Peptide

<400> SEQUENCE: 35

Val Phe
1

<210> SEQ ID NO 36
<211> LENGTH: 3
<212> TYPE: PRT
<213> ORGANISM: Artificial sequence
<220> FEATURE:
```

```
<223> OTHER INFORMATION: Synthetic Peptide

<400> SEQUENCE: 36

Val Phe Thr
1

<210> SEQ ID NO 37
<211> LENGTH: 4
<212> TYPE: PRT
<213> ORGANISM: Artificial sequence
<220> FEATURE:
<223> OTHER INFORMATION: Synthetic Peptide

<400> SEQUENCE: 37

Val Phe Thr Pro
1

<210> SEQ ID NO 38
<211> LENGTH: 5
<212> TYPE: PRT
<213> ORGANISM: Artificial sequence
<220> FEATURE:
<223> OTHER INFORMATION: Synthetic Peptide

<400> SEQUENCE: 38

Val Phe Thr Pro Pro
1               5

<210> SEQ ID NO 39
<211> LENGTH: 5
<212> TYPE: PRT
<213> ORGANISM: Artificial sequence
<220> FEATURE:
<223> OTHER INFORMATION: Synthetic Peptide

<400> SEQUENCE: 39

Phe Thr Pro Pro Ser
1               5

<210> SEQ ID NO 40
<211> LENGTH: 4
<212> TYPE: PRT
<213> ORGANISM: Artificial sequence
<220> FEATURE:
<223> OTHER INFORMATION: Synthetic Peptide

<400> SEQUENCE: 40

Phe Thr Pro Pro
1

<210> SEQ ID NO 41
<211> LENGTH: 3
<212> TYPE: PRT
<213> ORGANISM: Artificial sequence
<220> FEATURE:
<223> OTHER INFORMATION: Synthetic Peptide

<400> SEQUENCE: 41

Phe Thr Pro
1

<210> SEQ ID NO 42
<211> LENGTH: 2
<212> TYPE: PRT
<213> ORGANISM: Artificial sequence
<220> FEATURE:
<223> OTHER INFORMATION: Synthetic Peptide
```

```
<400> SEQUENCE: 42

Phe Thr
1

<210> SEQ ID NO 43
<211> LENGTH: 4
<212> TYPE: PRT
<213> ORGANISM: Artificial sequence
<220> FEATURE:
<223> OTHER INFORMATION: Synthetic Peptide

<400> SEQUENCE: 43

Thr Pro Pro Ser
1

<210> SEQ ID NO 44
<211> LENGTH: 3
<212> TYPE: PRT
<213> ORGANISM: Artificial sequence
<220> FEATURE:
<223> OTHER INFORMATION: Synthetic Peptide

<400> SEQUENCE: 44

Thr Pro Pro
1

<210> SEQ ID NO 45
<211> LENGTH: 2
<212> TYPE: PRT
<213> ORGANISM: Artificial sequence
<220> FEATURE:
<223> OTHER INFORMATION: Synthetic Peptide

<400> SEQUENCE: 45

Thr Pro
1

<210> SEQ ID NO 46
<211> LENGTH: 3
<212> TYPE: PRT
<213> ORGANISM: Artificial sequence
<220> FEATURE:
<223> OTHER INFORMATION: Synthetic Peptide

<400> SEQUENCE: 46

Pro Pro Ser
1

<210> SEQ ID NO 47
<211> LENGTH: 2
<212> TYPE: PRT
<213> ORGANISM: Artificial sequence
<220> FEATURE:
<223> OTHER INFORMATION: Synthetic Peptide

<400> SEQUENCE: 47

Pro Pro
1

<210> SEQ ID NO 48
<211> LENGTH: 2
<212> TYPE: PRT
<213> ORGANISM: Artificial sequence
<220> FEATURE:
<223> OTHER INFORMATION: Synthetic Peptide
```

```
<400> SEQUENCE: 48

Pro Ser
1

<210> SEQ ID NO 49
<211> LENGTH: 3
<212> TYPE: PRT
<213> ORGANISM: Artificial sequence
<220> FEATURE:
<223> OTHER INFORMATION: Synthetic Peptide

<400> SEQUENCE: 49

Arg Phe Gln
1

<210> SEQ ID NO 50
<211> LENGTH: 3
<212> TYPE: PRT
<213> ORGANISM: Artificial sequence
<220> FEATURE:
<223> OTHER INFORMATION: Synthetic Peptide

<400> SEQUENCE: 50

Phe Gln Leu
1

<210> SEQ ID NO 51
<211> LENGTH: 2
<212> TYPE: PRT
<213> ORGANISM: Artificial sequence
<220> FEATURE:
<223> OTHER INFORMATION: Synthetic Peptide

<400> SEQUENCE: 51

Phe Gln
1

<210> SEQ ID NO 52
<211> LENGTH: 2
<212> TYPE: PRT
<213> ORGANISM: Artificial sequence
<220> FEATURE:
<223> OTHER INFORMATION: Synthetic Peptide

<400> SEQUENCE: 52

Gln Leu
1

<210> SEQ ID NO 53
<211> LENGTH: 5
<212> TYPE: PRT
<213> ORGANISM: Artificial sequence
<220> FEATURE:
<223> OTHER INFORMATION: Synthetic Peptide

<400> SEQUENCE: 53

Gln Leu Asp Asp Val
1               5

<210> SEQ ID NO 54
<211> LENGTH: 4
<212> TYPE: PRT
<213> ORGANISM: Artificial sequence
<220> FEATURE:
<223> OTHER INFORMATION: Synthetic Peptide

<400> SEQUENCE: 54
```

Gln Leu Asp Asp
1

<210> SEQ ID NO 55
<211> LENGTH: 3
<212> TYPE: PRT
<213> ORGANISM: Artificial sequence
<220> FEATURE:
<223> OTHER INFORMATION: Synthetic Peptide

<400> SEQUENCE: 55

Gln Leu Asp
1

<210> SEQ ID NO 56
<211> LENGTH: 2
<212> TYPE: PRT
<213> ORGANISM: Artificial sequence
<220> FEATURE:
<223> OTHER INFORMATION: Synthetic Peptide

<400> SEQUENCE: 56

Gln Leu
1

<210> SEQ ID NO 57
<211> LENGTH: 5
<212> TYPE: PRT
<213> ORGANISM: Artificial sequence
<220> FEATURE:
<223> OTHER INFORMATION: Synthetic Peptide

<400> SEQUENCE: 57

Leu Asp Asp Val Glu
1               5

<210> SEQ ID NO 58
<211> LENGTH: 4
<212> TYPE: PRT
<213> ORGANISM: Artificial sequence
<220> FEATURE:
<223> OTHER INFORMATION: Synthetic Peptide

<400> SEQUENCE: 58

Leu Asp Asp Val
1

<210> SEQ ID NO 59
<211> LENGTH: 3
<212> TYPE: PRT
<213> ORGANISM: Artificial sequence
<220> FEATURE:
<223> OTHER INFORMATION: Synthetic Peptide

<400> SEQUENCE: 59

Leu Asp Asp
1

<210> SEQ ID NO 60
<211> LENGTH: 2
<212> TYPE: PRT
<213> ORGANISM: Artificial sequence
<220> FEATURE:
<223> OTHER INFORMATION: Synthetic Peptide

<400> SEQUENCE: 60

Leu Asp
1

<210> SEQ ID NO 61
<211> LENGTH: 4
<212> TYPE: PRT
<213> ORGANISM: Artificial sequence
<220> FEATURE:
<223> OTHER INFORMATION: Synthetic Peptide

<400> SEQUENCE: 61

Asp Asp Val Glu
1

<210> SEQ ID NO 62
<211> LENGTH: 3
<212> TYPE: PRT
<213> ORGANISM: Artificial sequence
<220> FEATURE:
<223> OTHER INFORMATION: Synthetic Peptide

<400> SEQUENCE: 62

Asp Asp Val
1

<210> SEQ ID NO 63
<211> LENGTH: 2
<212> TYPE: PRT
<213> ORGANISM: Artificial sequence
<220> FEATURE:
<223> OTHER INFORMATION: Synthetic Peptide

<400> SEQUENCE: 63

Asp Asp
1

<210> SEQ ID NO 64
<211> LENGTH: 3
<212> TYPE: PRT
<213> ORGANISM: Artificial sequence
<220> FEATURE:
<223> OTHER INFORMATION: Synthetic Peptide

<400> SEQUENCE: 64

Asp Val Glu
1

<210> SEQ ID NO 65
<211> LENGTH: 2
<212> TYPE: PRT
<213> ORGANISM: Artificial sequence
<220> FEATURE:
<223> OTHER INFORMATION: Synthetic Peptide

<400> SEQUENCE: 65

Asp Val
1

<210> SEQ ID NO 66
<211> LENGTH: 2
<212> TYPE: PRT
<213> ORGANISM: Artificial sequence
<220> FEATURE:
<223> OTHER INFORMATION: Synthetic Peptide

<400> SEQUENCE: 66

Val Glu

```
<210> SEQ ID NO 67
<211> LENGTH: 5
<212> TYPE: PRT
<213> ORGANISM: Artificial sequence
<220> FEATURE:
<223> OTHER INFORMATION: Synthetic Peptide

<400> SEQUENCE: 67

Arg Phe Gln Leu Thr
1               5

<210> SEQ ID NO 68
<211> LENGTH: 5
<212> TYPE: PRT
<213> ORGANISM: Artificial sequence
<220> FEATURE:
<223> OTHER INFORMATION: Synthetic Peptide

<400> SEQUENCE: 68

Phe Gln Leu Thr Glu
1               5

<210> SEQ ID NO 69
<211> LENGTH: 4
<212> TYPE: PRT
<213> ORGANISM: Artificial sequence
<220> FEATURE:
<223> OTHER INFORMATION: Synthetic Peptide

<400> SEQUENCE: 69

Phe Gln Leu Thr
1

<210> SEQ ID NO 70
<211> LENGTH: 4
<212> TYPE: PRT
<213> ORGANISM: Artificial sequence
<220> FEATURE:
<223> OTHER INFORMATION: Synthetic Peptide

<400> SEQUENCE: 70

Gln Leu Thr Glu
1

<210> SEQ ID NO 71
<211> LENGTH: 3
<212> TYPE: PRT
<213> ORGANISM: Artificial sequence
<220> FEATURE:
<223> OTHER INFORMATION: Synthetic Peptide

<400> SEQUENCE: 71

Gln Leu Thr
1

<210> SEQ ID NO 72
<211> LENGTH: 3
<212> TYPE: PRT
<213> ORGANISM: Artificial sequence
<220> FEATURE:
<223> OTHER INFORMATION: Synthetic Peptide

<400> SEQUENCE: 72

Leu Thr Glu
1
```

```
<210> SEQ ID NO 73
<211> LENGTH: 2
<212> TYPE: PRT
<213> ORGANISM: Artificial sequence
<220> FEATURE:
<223> OTHER INFORMATION: Synthetic Peptide

<400> SEQUENCE: 73

Leu Thr
1

<210> SEQ ID NO 74
<211> LENGTH: 2
<212> TYPE: PRT
<213> ORGANISM: Artificial sequence
<220> FEATURE:
<223> OTHER INFORMATION: Synthetic Peptide

<400> SEQUENCE: 74

Thr Glu
1
```